US012583967B2

(12) United States Patent
Kinbara et al.

(10) Patent No.: US 12,583,967 B2

(45) Date of Patent: Mar. 24, 2026

(54) BRANCHED TYPE HETERO MONODISPERSED POLYETHYLENE GLYCOL, PRODUCTION METHOD THEREOF, AND CONJUGATE THEREOF

(71) Applicants: TOKYO INSTITUTE OF TECHNOLOGY, Tokyo (JP); NOF CORPORATION, Tokyo (JP)

(72) Inventors: Kazushi Kinbara, Tokyo (JP); Tomoki Uruga, Tsukuba (JP); Tomoyuki Ohtake, Tsukuba (JP)

(73) Assignees: TOKYO INSTITUTE OF TECHNOLOGY, Tokyo (JP); NOF CORPORATION, Tokyo (JP)

( * ) Notice: Subject to any disclaimer, the term of this patent is extended or adjusted under 35 U.S.C. 154(b) by 424 days.

(21) Appl. No.: 18/168,119

(22) Filed: Feb. 13, 2023

(65) Prior Publication Data

US 2023/0192952 A1 Jun. 22, 2023

Related U.S. Application Data

(62) Division of application No. 16/338,873, filed as application No. PCT/JP2017/036479 on Oct. 6, 2017, now Pat. No. 11,613,607.

(30) Foreign Application Priority Data

Oct. 7, 2016 (JP) ................................ 2016-198654

(51) Int. Cl.
*C08G 65/333* (2006.01)
*A61K 47/60* (2017.01)
*C07C 217/28* (2006.01)

(52) U.S. Cl.
CPC ........ *C08G 65/33396* (2013.01); *A61K 47/60* (2017.08); *C07C 217/28* (2013.01)

(58) Field of Classification Search
None
See application file for complete search history.

(56) References Cited

U.S. PATENT DOCUMENTS

| | | | |
|---|---|---|---|
| 6,113,906 | A | 9/2000 | Greenwald et al. |
| 2003/0065134 | A1 | 4/2003 | Sakanoue et al. |
| 2003/0143596 | A1 | 7/2003 | Bentley et al. |
| 2005/0171291 | A1 | 8/2005 | Kozlowski et al. |
| 2005/0288490 | A1 | 12/2005 | Nakamoto et al. |

(Continued)

FOREIGN PATENT DOCUMENTS

| | | | |
|---|---|---|---|
| CN | 1400232 | A | 3/2003 |
| CN | 101045164 | A | 10/2007 |

(Continued)

OTHER PUBLICATIONS

Wawro, et al., "Chromatography-free synthesis of monodisperse oligo(ethylene glycol) mono-p-toluenesulfonates and quantitative analysis of oligomer purity", Polymer Chemistry, 7, 2389, 2016 (Year: 2016).*

(Continued)

*Primary Examiner* — Christopher M Rodd
(74) *Attorney, Agent, or Firm* — Sughrue Mion, PLLC

(57) ABSTRACT

A method of producing a compound represented by formula (3):

(3)

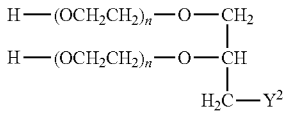

includes: step (1) of performing coupling of a monodispersed polyethylene glycol derivative represented by formula (4) shown below with a compound represented by formula (5) shown below using a base catalyst having a pKa in an aqueous solution of 15 to 20 to obtain a compound represented by formula (6) shown below, step (2) of deprotecting the protective group A of the compound represented by the formula (6) to obtain a compound represented by formula (7) shown below, and step (3) of subjecting the compound represented by the formula (7) to separatory purification; and step (4) of subjecting the compound represented by the formula (7) to deprotection treatment or reduction treatment to obtain the compound represented by formula (3), in an order described above, where $Y^2$, n, A, B, and Z are as defined herein:

(4)

$$A—(OCH_2CH_2)_n—B$$

(5)

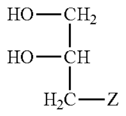

(6)

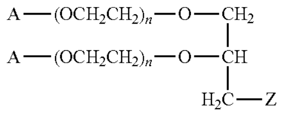

(7)

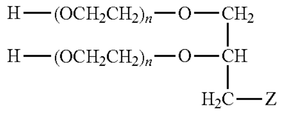

4 Claims, No Drawings

(56) References Cited

U.S. PATENT DOCUMENTS

| | | | |
|---|---|---|---|
| 2006/0073113 A1 | 4/2006 | Nakamoto et al. | |
| 2006/0178475 A1 | 8/2006 | Bentley et al. | |
| 2010/0004428 A1 | 1/2010 | Kozlowski et al. | |
| 2011/0077362 A1 | 3/2011 | Bentley et al. | |
| 2012/0077988 A1* | 3/2012 | Yamamoto ....... | G01N 33/54353 568/607 |
| 2012/0322134 A1 | 12/2012 | Bentley et al. | |
| 2012/0322955 A1 | 12/2012 | Yoshioka et al. | |
| 2013/0052130 A1 | 2/2013 | Davis et al. | |
| 2013/0295639 A1 | 11/2013 | Bentley et al. | |
| 2014/0199750 A1 | 7/2014 | Weng et al. | |
| 2014/0329994 A1 | 11/2014 | Bentley et al. | |
| 2016/0032049 A1 | 2/2016 | Bentley et al. | |
| 2017/0312363 A1 | 11/2017 | Weng et al. | |
| 2018/0214561 A1 | 8/2018 | Weng et al. | |
| 2018/0312466 A1 | 11/2018 | Yamamoto et al. | |

FOREIGN PATENT DOCUMENTS

| | | | |
|---|---|---|---|
| CN | 101831067 | A | 9/2010 |
| CN | 102985462 | A | 3/2013 |
| CN | 103044676 | A | 4/2013 |
| CN | 104530415 | A | 4/2015 |
| EP | 1 019 446 | B1 | 3/2007 |
| EP | 2 586 811 | A1 | 5/2013 |
| JP | 2001-519784 | A | 10/2001 |
| JP | 2004-197077 | A | 7/2004 |
| JP | 2005-508421 | A | 3/2005 |
| JP | 2007-538111 | A | 12/2007 |
| JP | 2012-25932 | A | 2/2012 |
| WO | 98/41562 | A1 | 9/1998 |
| WO | 2011162252 | A1 | 12/2011 |
| WO | 2012/133490 | A1 | 10/2012 |

OTHER PUBLICATIONS

Office Action dated Dec. 2, 2020, issued by the State Intellectual Property Office of P.R. China in Chinese Patent Application No. 201780062226.6.

Robert Y. Zhao et al. "Synthesis and Evaluation of Hydrophilic Linkers for Antibody—Maytansinoid Conjugates" Journal of Medicinal Chemistry, vol. 54, 2011 (pp. 3606-3623).

International Search Report (PCT/ISA/210), issued by International Searching Authority in corresponding International Application No. PCT/JP2017/036479, on Jan. 9, 2018.

Communication dated Oct. 4, 2021, from the Japanese Patent Office in Application No. 2017-195773.

Franco Dosio et al. "Immunotoxins and Anticancer Drug Conjugate Assemblies: The Role of the Linkage between Components" Toxins, vol. 3, 2011 (pp. 848-879).

Written Opinion (PCT/ISA/237) issued by the International Searching Authority in corresponding International Application No. PCT/JP2017/036479, on Jan. 9, 2018.

Search Report issued Mar. 17, 2020 by the European Patent Office in European Patent Application No. 17858528.7.

Office Action issued Jun. 17, 2021, issued by the Japan Patent Office in Japanese Patent Application No. 2017-195773.

Office Action dated Feb. 23, 2021, issued by the India Intellectual Property Office in Indian Patent Application No. 201947013859.

Office Action issued Jul. 29, 2025 by the United States Patent and Trademark Office in U.S. Appl. No. 18/168,162.

* cited by examiner

BRANCHED TYPE HETERO MONODISPERSED POLYETHYLENE GLYCOL, PRODUCTION METHOD THEREOF, AND CONJUGATE THEREOF

CROSS REFERENCE TO RELATED APPLICATIONS

This application is a Divisional Application of Ser. No. 16/338,873 filed Apr. 2, 2019, which is a National Stage of International Application No. PCT/JP2017/036479 filed Oct. 6, 2017, which claims priority based on Japanese Patent Application No. 2016-198654 filed Oct. 7, 2016. The contents of all of the prior applications are incorporated herein by reference in their entireties.

TECHNICAL FIELD

The present invention relates to a branched type hetero monodispersed polyethylene glycol, an intermediate for production of the branched type hetero monodispersed polyethylene glycol and methods for producing these, and a branched type hetero monodispersed polyethylene glycol conjugate. More specifically, it relates to a branched type hetero monodispersed polyethylene glycol, which is used for modification of a biofunctional polymer, a drug or a drug carrier in a drug delivery system, a material or device for diagnosis and the like and in particular, which is useful as a linker for antibody-drug conjugate.

BACKGROUND ART

In recent years, an antibody-drug conjugate (Antibody-Drug Conjugate: ADC), in which a drug is conjugated to an antibody through a linker and which is capable of actively transporting the drug to an antigen-presenting cell, is practically used and has attracted high attention in the field of pharmaceuticals (Toxins, 2011, 3, p. 848-883 (Non-Patent Document 1), J. Med. Chem., 2011, 54, p. 3606-3623 (Non-Patent Document 2)).

Since many of the drugs are commonly hydrophobic, when they are used as ADC, aggregation sometimes occurs. Therefore, one of the linkers which have been investigated is a hetero type monodispersed polyethylene glycol which is a hydrophilic linker.

The hetero type monodispersed polyethylene glycol means a compound which has functional groups different from each other at both terminals (hetero type) in order to separately conjugate a drug and an antibody to each of the terminals and contains 90% or more of a compound having a specific ethylene glycol chain length in order to simplify the drug application and the production, purification and analysis of ADC.

In the ADC described above, since an antibody and a drug are separately conjugated to each of the terminals of the hetero type monodispersed polyethylene glycol described above as a linker, when a compound having the mutually same functional groups at the both terminals (homo type polyethylene glycol or the like) is present as an impurity in the hetero type monodispersed polyethylene glycol described above, a compound having two antibodies conjugated or a compound having two drugs conjugated is generated. The compound having two antibodies conjugated does not exhibit the effect of ADC because the drug is not conjugated. The compound having two drugs conjugated is transported to a position other than the antigen-presenting cell to be a cause of side effects because the antibody is not conjugated. Further, the same problems as described above also arise in the case where other hetero type compound having functional groups in combination different from a hetero type polyethylene glycol having the desired functional groups is present as an impurity, because a compound losing either the desired antibody or the desired drug is generated. Therefore, from the standpoint of use and effect of the drug, it can be said to be important that the hetero type monodispersed polyethylene glycol described above contains a hetero type polyethylene glycol having the different functional groups each other at the both terminals thereof in high purity, that is, the functional group purity is high.

Further, in recent years, for the purpose of increasing the transport efficiency of the drug in ADC described above, it has been desired to use ADC in which a plurality of drugs are conjugated to an antibody and a method of using a linker having a branched type structure has been tried as one means.

For example, in Patent Document 1 (US20130052130A1) a branched type hetero monodispersed polyethylene glycol in which three of four ethylene glycol chains described above are introduced by conjugating the monodispersed polyethylene glycols to a branching site composed of tris-hydroxyaminomethane (Tris) or an amino acid, for example, lysine is disclosed.

Further, in Patent Document 2 (CN104530415A) a branched type hetero monodispersed polyethylene glycol in which three ethylene glycol chains described above are introduced by conjugating the monodispersed polyethylene glycols to a branching site composed of glycerol or thioglycerol is disclosed.

In Patent Document 1 and Patent Document 2, in common, the monodispersed polyethylene glycols are conjugated to all conjugating points of the branch site and a functional group conjugatable to an antibody or a drug is conjugated to the end of the polyethylene glycol. This can be schematically shown as below:

$$(X\text{-}PEG^1\text{-})_n\text{-}B\text{-}PEG^2\text{-}Y$$

(in the formula, X and Y each represents a functional group different from each other, and n represents an integer of 2 or 3. B represents a branch skeleton. $PEG^1$ and $PEG^2$ each represents a straight-chain type monodispersed polyethylene glycol.)

In Patent Document 1 and Patent Document 2, as a method of obtaining the branched type hetero monodispersed polyethylene glycol described above, a method in which two kinds of straight-chain type monodispersed polyethylene glycols having the terminal functional groups different form each other (X-$PEG^1$ and $PEG^2$-Y) are prepared, and first X-$PEG^1$ and a branch site are reacted and then $PEG^2$-Y is reacted or first $PEG^2$-Y and a branch site are reacted and then X-$PEG^1$ is reacted is described. An example of the case where first $PEG^2$-Y and a branch site are reacted is shown in the formulae below.

First Step $$B+PEG^2\text{-}Y\rightarrow B\text{-}PEG^2\text{-}Y$$

Second Step $$X\text{-}PEG^1+B\text{-}PEG^2\text{-}Y\rightarrow(X\text{-}PEG^1\text{-})_n\text{-}B\text{-}PEG^2\text{-}Y$$

(in the formulae, X and Y each represents a functional group different from each other, and n represents an integer of 2 or 3. B represents a branch site. $PEG^1$ and $PEG^2$ each represents a straight-chain type monodispersed polyethylene glycol.)

In the production of branched type hetero monodispersed polyethylene glycol described above, there is a possibility of remaining $PEG^2$-Y in the reaction between the branch site B and $PEG^2$-Y in the first step as shown in the formula below. This compound has the same functional group as the desired branched type hetero monodispersed polyethylene glycol at only one terminal. Therefore, when the branched type hetero monodispersed polyethylene glycol containing the monodispersed polyethylene glycol excessively added is used for the production of ADC, because of low functional group purity, a compound losing either the desired antibody or the desired drug is generated to cause decrease in effectiveness as drug.

$$B+PEG^2\text{-}Y \rightarrow B\text{-}PEG^2\text{-}Y+PEG^2\text{-}Y$$

Further, there is a possibility of remaining X-$PEG^1$ excessively added in the reaction with X-$PEG^1$ in the second step as shown in the formula below. This compound has the same functional group as the desired branched type hetero monodispersed polyethylene glycol at only one terminal. Therefore, when the branched type hetero monodispersed polyethylene glycol containing the monodispersed polyethylene glycol excessively added is used for the production of ADC, because of low functional group purity, a compound losing either the desired antibody or the desired drug is generated to cause decrease in effectiveness as drug.

$$X\text{-}PEG^1+B\text{-}PEG^2\text{-}Y \rightarrow (X\text{-}PEG^1\text{-})_n\text{-}B\text{-}PEG^2\text{-}Y+X\text{-}PEG^1$$

PRIOR ART DOCUMENTS

Patent Documents

Patent Document 1: US20130052130A1
Patent Document 2: CN104530415A

Non-Patent Document

Non-Patent Document 1: Toxins, 2011, 3, p. 848-883
Non-Patent Document 2: J. Med. Chem., 2011, 54, p. 3606-3623

SUMMARY OF THE INVENTION

Problems to be Solved by the Invention

As described above, because in the branched type hetero monodispersed polyethylene glycols described in Patent Document 1 and Patent Document 2 it is necessary to react two kinds of straight-chain type monodispersed polyethylene glycols having different terminal functional groups in the two steps, due to the remaining of the straight-chain type monodispersed polyethylene glycol excessively added, the purity of the desired branched type hetero monodispersed polyethylene glycol decreases and there is a possibility that a problem may arise in view of use and effect of drug.

Further, as a method of purifying the branched type hetero monodispersed polyethylene glycol, recrystallization, column purification and the like are exemplified. In Patent Document 1 and Patent Document 2, the monodispersed polyethylene glycol excessively added ($PEG^2$-Y and X-$PEG^1$) is removed by column chromatography. However, since the monodispersed polyethylene glycols having the same terminal functional group have similar physical properties even when the chain lengths are different, the column purification is difficult to cause decrease in the yield.

An object of the invention is to obtain a branched type hetero monodispersed polyethylene glycol having functional groups different from each other at the both terminals thereof in high purity, an intermediate for production of the branched type hetero monodispersed polyethylene glycol described above, a hetero type monodispersed polyethylene glycol conjugate in which the branched type hetero monodispersed polyethylene glycol and a biofunctional molecule are conjugated, and an intermediate for production of the branched type hetero monodispersed polyethylene glycol described above.

Means for Solving the Problems

As a result of the intensive investigations to achieve the object described above, the inventors have found that a branched type monodispersed polyethylene glycol which has functional groups different from each other at the both terminals thereof in high purity and in which a monodispersed polyethylene glycol is not conjugated to one of three conjugating points of the branch site as shown in formula (1) can be obtained. Further, the inventors have found that a branched type hetero monodispersed polyethylene glycol having functional groups different from each other at the both terminals thereof in high purity can be obtained only with a simple separatory extraction and without using a purification method, for example, column chromatography by synthesizing an intermediate for producing the branched type hetero monodispersed polyethylene glycol described above using a specific functional group at the terminal to complete the invention.

Thus, the present invention provides the following (1) to (11).

(1) A branched type hetero monodispersed polyethylene glycol represented by formula (1):

$$\{X^1—L^1—(OCH_2CH_2)_n—L^2\}_2—E—L^3—Y^1 \qquad (1)$$

(in formula (1), $X^1$ and $Y^1$ each represents an atomic group containing at least a functional group capable of reacting with a functional group present in a biofunctional molecule to form a covalent bond, provided that the functional group contained in the atomic group $X^1$ and the functional group contained in the atomic group $Y^1$ are different from each other, n is an integer of 6 to 30, E is a branch site having a divalent bond valence number to $L^2$ and a monovalent bond valence number to $L^3$ and represents a glycerol site, $L^1$ and $L^2$ each independently represents a single bond or a divalent organic group, and $L^3$ represents a single bond, $-L^4-(CH_2)_{m1}—$ or $-L^4-(CH_2)_{m2}-L^5-(CH_2)_{m3}—$, $L^4$ represents any of an ether bond, an amide bond and a urethane bond, $L^5$ represents an amide bond or a urethane bond, and m1, m2 and m3 each independently represents an integer of 1 to 5.)

(2) The branched type hetero monodispersed polyethylene glycol of (1), wherein $L^3$ represents $-L^4-(CH_2)_{m1}—$ or $-L^4-(CH_2)_{m2}-L^5-(CH_2)_{m3}—$, $L^4$ represents any of an ether bond, an amide bond and a urethane bond, $L^5$ represents an amide bond or a urethane bond, and m1, m2 and m3 each independently represents an integer of 1 to 5.

(3) The branched type hetero monodispersed polyethylene glycol of (1) or (2), wherein $L^2$ in formula (1) is an ether bond.

(4) The branched type hetero monodispersed polyethylene glycol of (1) or (2), which is represented by formula (2):

(2)

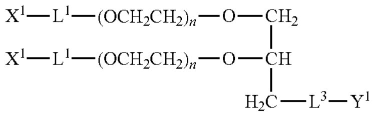

(in formula (2), $X^1$ and $Y^1$ each represents an atomic group containing at least a functional group capable of reacting with a functional group present in a biofunctional molecule to form a covalent bond, provided that the functional group contained in the atomic group $X^1$ and the functional group contained in the atomic group $Y^1$ are different from each other, n is an integer of 6 to 30, $L^1$ represents a single bond or a divalent organic group, and L3 represents a single bond, $-L^4-(CH_2)_{m1}-$ or $-L^4-(CH_2)_{m2}-L^5-(CH_2)_{m3}-$, $L^4$ represents any of an ether bond, an amide bond and a urethane bond, $L^5$ represents an amide bond or a urethane bond, and m1, m2 and m3 each independently represents an integer of 1 to 5.)

(5) An intermediate for production of the branched type hetero monodispersed polyethylene glycol of (4), which is represented by formula (3):

(3)

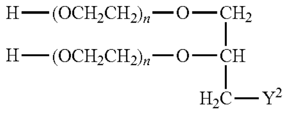

(in formula (3), n represents an integer of 6 to 30, and $Y^2$ represents $-NH_2$ or $-O-(CH_2)_{m4}-NH_2$, and m4 represents an integer of 1 to 5.)

(6) A method of producing the intermediate for production of the branched type hetero monodispersed polyethylene glycol of (5) comprising:

step (1) of performing coupling of a monodispersed polyethylene glycol derivative represented by formula (4) shown below with a compound represented by formula (5) shown below using a base catalyst having a pKa in an aqueous solution of 15 to 20 to obtain a compound represented by formula (6) shown below, $$A\text{-}(OCH_2CH_2)_n\text{—}B \quad (4)$$

(in formula (4),

A represents a protective group for a hydroxyl group,

B represents a leaving group, and n represents an integer of 6 to 30), (5)

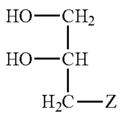

(in formula (5),

Z represents $-Z^1$ or $-O-(CH_2)_{m5}-Z^1$, $Z^1$ represents any of a protected form of an amino group, an azide group and a cyano group, and m5 represents an integer of 1 to 5), (6)

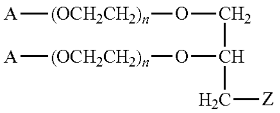

(in formula (6),

A represents a protective group for a hydroxyl group,

Z represents $-Z^1$ or $-O-(CH_2)_{m5}-Z^1$, $Z^1$ represents any of a protected form of an amino group, an azide group and a cyano group, and m5 represents an integer of 1 to 5, and n represents an integer of 6 to 30);

step (2) of deprotecting the protective group A of the compound represented by formula (6) to obtain a compound represented by formula (7) shown below, (7)

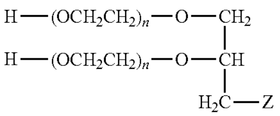

(in formula (7),

Z represents $-Z^1$ or $-O-(CH_2)_{m5}-Z^1$, $Z^1$ represents any of a protected form of an amino group, an azide group and a cyano group, and m5 represents an integer of 1 to 5, and n represents an integer of 6 to 30);

step (3) of subjecting the compound represented by formula (7) to separatory purification; and step (4) of subjecting the compound represented by formula (7) to deprotection treatment or reduction treatment to obtain the intermediate for production of the branched type hetero monodispersed polyethylene glycol represented by formula (3), in the order described above.

(7) The method of (6), wherein the base catalyst is any of potassium hydroxide, sodium hydroxide, potassium tert-butoxide and sodium tert-butoxide.

(8) A branched type hetero monodispersed polyethylene glycol conjugate in which a biofunctional molecule is conjugated to the branched type hetero monodispersed polyethylene glycol of any one of (1) to (4).

(9) An intermediate for production of the branched type hetero monodispersed polyethylene glycol of (4), which is represented by formula (40):

(40)

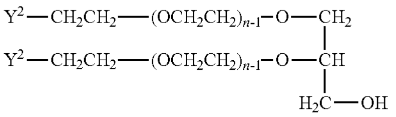

(in formula (40), n represents an integer of 6 to 30, and $Y^2$ represents $—NH_2$ or $—O—(CH_2)_{m4}—NH_2$, and m4 represents an integer of 1 to 5.)

(10) A method of producing the intermediate for production of the branched type hetero monodispersed polyethylene glycol of (9) comprising:

step (1') of performing coupling of a monodispersed polyethylene glycol derivative represented by formula (41) shown below with a compound represented by formula (42) shown below using a base catalyst having a pKa in an aqueous solution of 15 to 20 to obtain a compound represented by formula (43) shown below, $$Z—CH_2CH_2—(OCH_2CH_2)_{n-1}—B \quad (41)$$

(in formula (41),

Z represents $—Z^1$ or $—O—(CH_2)_{m5}—Z^1$, $Z^1$ represents any of a protected form of an amino group, an azide group and a cyano group, and m5 represents an integer of 1 to 5, B represents a leaving group, and n represents an integer of 6 to 30), (42)

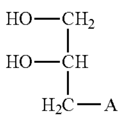

(in formula (42),

A represents a protective group for a hydroxyl group), (43)

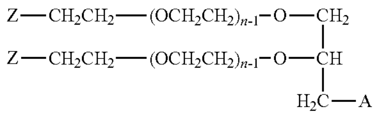

(in formula (43),

A represents a protective group for a hydroxyl group,

Z represents $—Z^1$ or $—O—(CH_2)_{m5}—Z^1$, $Z^1$ represents any of a protected form of an amino group, an azide group and a cyano group, and m5 represents an integer of 1 to 5, and n represents an integer of 6 to 30);

step (2') of deprotecting the protective group A of the compound represented by formula (43) to obtain a compound represented by formula (44) shown below, (44)

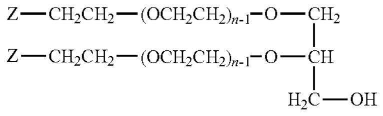

(in formula (44),

Z represents $—Z^1$ or $—O—(CH_2)_{m5}—Z^1$, $Z^1$ represents any of a protected form of an amino group, an azide group and a cyano group, and m5 represents an integer of 1 to 5, and n represents an integer of 6 to 30);

step (3') of subjecting the compound represented by formula (44) to deprotection treatment or reduction treatment to obtain the intermediate for production of the branched type hetero monodispersed polyethylene glycol represented by formula (40); and step (4') of subjecting the compound represented by formula (40) to separatory purification, in the order described above.

(11) The method of (10), wherein the base catalyst is any of potassium hydroxide, sodium hydroxide, potassium tert-butoxide and sodium tert-butoxide.

Effect of the Invention

Since the compound represented by formula (1) described above or formula (2) described above of the invention has functional groups different from each other at the both terminals thereof in high purity, when it is used as ACD, generation of a compound losing either the desired antibody or the desired drug is suppressed so that the increase in the effect of ADC is expected.

Further, in the method of producing the compound represented by formula (1) described above or formula (2) described above of the invention, since a monodispersed polyethylene glycol is not conjugated to one of three conjugating points of the branch site, the compound represented by formula (1) described above or formula (2) described above having functional groups different from each other at the both terminals thereof in high purity can be easily obtained.

Moreover, in the method of producing the compound represented by formula (3) described above of the invention, since a side reaction is suppressed by using a specific base catalyst in step (1) described above and impurities derived from the compound represented by formula (4) described above excessively added in step (1) can be removed only with separatory purification by performing step (1) to step (4) described above in this order, the compound represented by formula (3) described above having high chain length purity and high functional group purity can be easily obtained.

Furthermore, since a side reaction is suppressed by using a specific base catalyst in step (1') described above and impurities derived from the compound represented by formula (41) described above excessively added in step (1') can be removed only with separatory purification by performing step (1') to step (4') described above in this order, the compound represented by formula (40) described above having high chain length purity and high functional group purity can be easily obtained.

MODE FOR CARRYING OUT THE INVENTION

Preferred embodiments of the invention will be described in detail hereinafter.

The branched type hetero monodispersed polyethylene glycol according to the invention is a compound which has two kinds of functional groups at the terminals in high purity and a monodispersed polyethylene glycol is not conjugated to one of three conjugating points of the branch site. Further, the terminal functional group of high purity means that purity of the compound having a specific combination of functional groups (hereinafter, referred to as functional group purity) is 95% or more. Moreover, a monodispersed polyethylene glycol means that purity of the compound having a specific ethylene glycol chain length (hereinafter, referred to as chain length purity) is 90% or more.

The branched type hetero monodispersed polyethylene glycol is represented by formula (1).

$$\{X^1—L^1—(OCH_2CH_2)_n—L^2\}_2 E—L^3—Y^1 \quad (1)$$

In formula (1), $X^1$ and $Y^1$ each represents an atomic group containing at least a functional group capable of reacting with a functional group present in a biofunctional molecule to form a covalent bond, provided that the functional group contained in the atomic group $X^1$ and the functional group contained in the atomic group $Y^1$ are different from each other. n represents a number of repeating units of a monodispersed polyethylene glycol and is an integer of 6 to 30. E is a branch site having a divalent bond valence number to $L^1$ and a monovalent bond valence number to $L^3$ and represents a glycerol site. $L^1$ and $L^2$ each independently represents a single bond or a divalent organic group. L3 represents a single bond, $-L^4-(CH_2)_{m1}—$ or $-L^4-(CH_2)_{m2}-L^5-(CH_2)_{m3}—$, $L^4$ represents any of an ether bond, an amide bond and a urethane bond, $L^5$ represents an amide bond or a urethane bond, and m1, m2 and m3 each independently represents an integer of 1 to 5.

In formula (1) described above, $X^1$ and $Y^1$ are functional groups different from each other and the functional group is not particularly limited as long as it is a functional group capable of forming a covalent bond by reacting with a functional group present in a biofunctional molecule (protein drug, polypeptide, enzyme, antibody, antibody drug, gene, nucleic acid compound including oligonucleic acid or the like, nucleic acid drug, anticancer drug, and other drugs, for example, low molecular weight drug), which is a target for modification by the branched type hetero monodispersed polyethylene glycol. Among them, $X^1$ and $Y^1$ each independently is preferably a functional group capable of reacting under mild conditions and with a high reaction efficiency with a group (for example, an amino group, a thiol group, an aldehyde group or a carboxyl group) present in a naturally occurring biofunctional molecule represented by protein or a group (for example, a maleimide group, a ketone group, an azide group or an alkynyl group) capable of artificially introducing into the biofunctional molecule. More specifically, it is preferably an aldehyde group, a maleimide group, a vinylsulfone group, an iodoacetamide group, a bromoacetamide group, an active ester group, an active carbonate group, a carboxyl group, an amino group, an aminooxy group, a thiol group, an allyl group, a vinyl group, an alkynyl group or an azide group. Further, taking the reaction efficiency and the like into consideration, $X^1$ and $Y^1$ each is more preferably a maleimide group, an active ester group, an active carbonate group, an alkynyl group, an azide group, an iodoacetamide group or a bromoacetamide group.

Further, $X^1$ and $Y^1$ each independently is preferably an aldehyde group, an active ester group, an active carbonate group, a carboxyl group or a ketone group in the case where the functional group present in the biofunctional molecule targeted is an amino group; a maleimide group, a vinylsulfone group, an iodoacetamide group, a bromoacetamide group, an allyl group or a vinyl group in the case where the functional group present in the biofunctional molecule targeted is a thiol group; an amino group in the case where the functional group present in the biofunctional molecule targeted is an aldehyde group or a ketone group; an amino group, an aminooxy group or a thiol group in the case where the functional group present in the biofunctional molecule targeted is a carboxyl group; a thiol group in the case where the functional group present in the biofunctional molecule targeted is a maleimide group; an alkynyl group in the case where the functional group present in the biofunctional molecule targeted is an azide group; and an azide group in the case where the functional group present in the biofunctional molecule targeted is an alkynyl group.

As to a preferred combination of $X^1$ and $Y^1$, for example, when $X^1$ is an active ester group, $Y^1$ is preferably a maleimide group, an azide group, an alkynyl group, an iodoacetamide group, a bromoacetamide group, a vinylsulfone group, an oxyamino group, a thiol group, an allyl group or a vinyl group; when $X^1$ is an active carbonate group, $Y^1$ is preferably a maleimide group, an azide group, an alkynyl group, an iodoacetamide group, a bromoacetamide group, a vinylsulfone group, an oxyamino group, a thiol group, an allyl group or a vinyl group; when $X^1$ is a maleimide group, $Y^1$ is preferably an active ester group, an active carbonate group, an azide group, an alkynyl group, an aldehyde group, a carboxyl group, an amino group, an oxyamino group or a ketone group; when $X^1$ is an azide group, $Y^1$ is preferably an active ester group, an active carbonate group, a maleimide group, an iodoacetamide group, a bromoacetamide group, an aldehyde group, a vinylsulfone group, a carboxyl group, an amino group, an oxyamino group, a thiol group, an allyl group, a vinyl group or a ketone group; when $X^1$ is an alkynyl group, $Y^1$ is preferably an active ester group, an active carbonate group, a maleimide group, an iodoacetamide group, a bromoacetamide group, an aldehyde group, a vinylsulfone group, a carboxyl group, an amino group, an oxyamino group, a thiol group, an allyl group, a vinyl group or a ketone group.

In formula (1) described above, $L^1$ is a linker responsible for the conjugate between the polyethylene glycol chain and $X^1$, is not particularly limited as long as it is a site composed of a covalent bond, and is preferably a single bond, a divalent saturated hydrocarbon group, a urethane bond, an amide bond, an ether bond, a carbonate bond or a divalent saturated hydrocarbon group containing a urethane bond, an amide bond, an ether bond or a carbonate bond. The saturated hydrocarbon group described above is preferably that containing 10 or less carbon atoms and includes, for example, a methylene group, an ethylene group, a trimethylene group, a propylene group, an isopropylene group, a tetramethylene group, a butylene group, an isobutylene group, a pentamethylene group and a hexamethylene group.

In formula (1), $L^3$ is a linker responsible for the conjugate between $Y^1$ and the branch site E and is represented by a single bond, $-L^4-(CH_2)_{m1}—$ or $-L^4-(CH_2)_{m2}-L^5-(CH_2)_{m3}—$. $L^4$ represents any of an ether bond, an amide bond and a urethane bond, $L^5$ represents an amide bond or a urethane bond, and m1, m2 and m3 each independently represents an integer of 1 to 5.

A preferred example of $L^3$ in the invention in which $L^4$ is an ether bond and $L^5$ is an amide bond is represented by any of the following formulae:

$$—O—(CH_2)_{m2}—C(O)NH—(CH_2)_{m3}— \quad (8)$$

$$—O—(CH_2)_{m2}—NHC(O)—(CH_2)_{m3}— \quad (9)$$

The maleimide group in the invention is a group represented by the following formula including $L^1$ or $L^3$ and is a group which reacts with a nucleophilic group, for example, a thiol group.

(10)

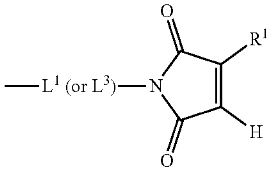

In formula (10) described above, $R^1$ is preferably a hydrogen atom or a methyl group, and more preferably a hydrogen atom.

In the case where $X^1$ or $Y^1$ is a maleimide group in the invention, a preferred example of $-L^1-X^1$ or $-L^3-Y^1$ is represented by the following formula:

(11)

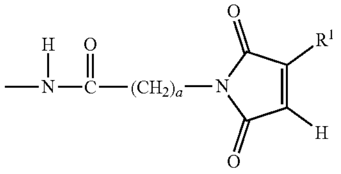

In formula (11) described above, a represents an integer of 1 to 5, and $R^1$ has the same meaning as $R^1$ in formula (10) described above.

The active ester group in the invention is a group represented by the following formula including $L^1$ or $L^3$ and reacts with a nucleophilic group, for example, an amino group.

(12)

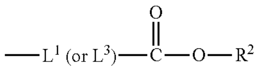

In formula (12) described above, $R^2$ is preferably a phenyl group, a 3-pyridyl group, a succinimide group, a 2-benzothiazole group or a 1-benzotriazole group, more preferably a succinimide group or a 1-benzotriazole group, and most preferably a succinimide group.

In the case where $X^1$ or $Y^1$ is an active ester group in the invention, a preferred example of $-L^1-X^1$ or $-L^3-Y^1$ is represented by the following formula:

(13)

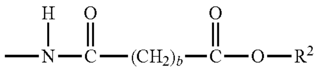

In formula (13) described above, b represents an integer of 1 to 5, and $R^2$ has the same meaning as $R^2$ in formula (12) described above.

The active carbonate group in the invention is a group represented by the following formula including $L^1$ or $L^3$ and reacts with a nucleophilic group, for example, an amino group.

(14)

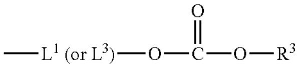

In formula (14) described above, $R^3$ is preferably a phenyl group, a 3-pyridyl group, a succinimide group, a 4-nitrophenyl group, a 2-benzothiazole group or a 1-benzotriazole group, more preferably a succinimide group or a 1-benzotriazole group, and most preferably a succinimide group.

In the case where $X^1$ or $Y^1$ is an active carbonate group in the invention, a preferred example of $-L^1-X^1$ or $-L^3-Y^1$ is represented by the following formula:

(15)

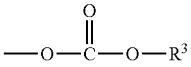

In formula (15) described above, $R^3$ has the same meaning as $R^3$ in formula (14) described above.

The alkynyl group in the invention is a group represented by any one of the following formulae including $L^1$ or $L^2$ and reacts with an azide group.

(16)

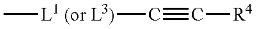

(17)

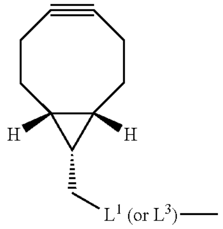

(18)

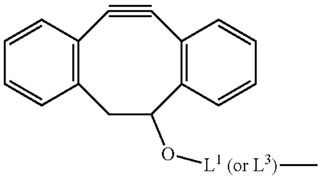

(19)

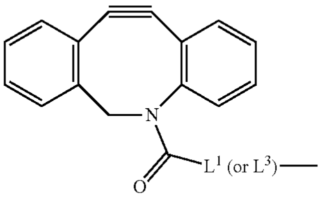

In the formula described above, $R^4$ is preferably a saturated hydrocarbon group having 8 or less carbon atoms or a hydrogen atom and more preferably a hydrogen atom.

In the case where $X^1$ or $Y^1$ is an alkynyl group in the invention, a preferred example of $-L^1-X^1$ or $-L^3-Y^1$ is represented by the following formulae:

(20)

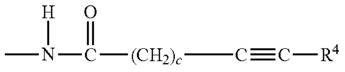

(21)

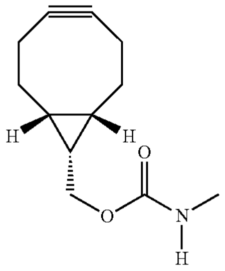

(22)

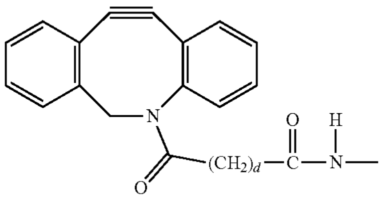

In formula (20) described above, c represents an integer of 2 to 5, and $R^4$ has the same meaning as $R^4$ in formula (21) described above. Further, in formula (22) described above, d represents an integer of 1 to 6.

$X^1$ or $Y^1$ in the case where $X^1$ or $Y^1$ is an iodoacetamide group or a bromoacetamide group in the invention is represented by the following formulae including $L^1$ or $L^3$ and reacts with a thiol group.

(23)

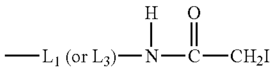

(24)

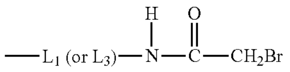

n represents a number of repeating units of a monodispersed polyethylene glycol and is an integer of 6 to 30. From the standpoint of using as a linker for ADC, n is preferably an integer of 6 to 24.

E is a branch site having a divalent bond valence number to $L^2$ and a monovalent bond valence number to $L^3$ and represents a glycerol site.

The glycerol site in the invention is represented by any one of the following formulae including $L^2$ and $L^3$ and from the standpoint of raw material purity, it is preferred to have the structure represented by formula (25).

(25)

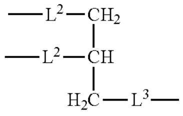

(26)

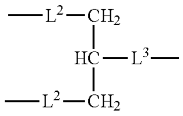

$L^2$ is a linker responsible for the conjugate between the polyethylene glycol chain and the branch site E, is not particularly limited as long as it is a site composed of a covalent bond, and includes, for example, a single bond, a divalent saturated hydrocarbon group, a urethane bond, an amide bond, an ether bond, a carbonate bond and a divalent saturated hydrocarbon group containing a urethane bond, an amide bond, an ether bond or a carbonate bond. $L^2$ is preferably any of a urethane bond, an amide bond and an ether bond, and from the standpoint of raw material purity, it is more preferably an ether bond. The saturated hydrocarbon group described above is preferably that containing 10 or less carbon atoms and includes, for example, a methylene group, an ethylene group, a trimethylene group, a propylene group, an isopropylene group, a tetramethylene group, a butylene group, an isobutylene group, a pentamethylene group and a hexamethylene group.

Preferred examples of the branched type hetero monodispersed polyethylene glycol represented by formula (1) described above include compounds represented by formula (28) shown below.

(28)

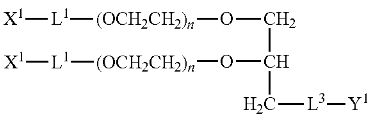

The intermediate for production of the branched type hetero monodispersed polyethylene glycol in the invention is represented by formula (29) shown below.

$$\{X^2—(OCH_2CH_2)_n—L^2\}_2 E—Y^2 \qquad (29)$$

In formula (29) described above, n represents an integer of 6 to 30. $X^2$ and $Y^2$ are functional groups different from each other, and $X^2$ represents a hydrogen atom or any of an amino group and carboxyl group containing a divalent saturated hydrocarbon group. $Y^2$ represents any of $—NH_2$, $—O—(CH_2)_{m4}—NH_2$, $—COOH$ and $—O—(CH_2)_{m6}—COOH$. m4 and m6 each represents an integer of 1 to 5. $L^2$ represents a divalent organic group. E is a branch site having a divalent bond valence number to $L^2$ and a monovalent bond valence number to $Y^2$ and represents a glycerol site.

In formula (29) described above, n represents a number of repeating units of a monodispersed polyethylene glycol and is an integer of 6 to 30. From the standpoint of using as a linker for ADC, n is preferably an integer of 6 to 24.

In formula (29) described above, $X^2$ is not particularly limited as long as it is a functional group capable of being converted to $X^1$ in formula (1), and is preferably a hydrogen atom or any of an amino group and carboxyl group containing a divalent saturated hydrocarbon group, more preferably a hydrogen atom. The saturated hydrocarbon group described above is preferably that containing 10 or less carbon atoms and includes, for example, a methylene group, an ethylene group, a trimethylene group, a propylene group, an isopropylene group, a tetramethylene group, a butylene group, an isobutylene group, a pentamethylene group and a hexamethylene group.

In formula (29) described above, $Y^2$ is not particularly limited as long as it is a functional group capable of being converted to $Y^1$ in formula (1), and is preferably any of $-NH_2$, $-O-(CH_2)_{m4}-NH_2$, $-COOH$ and $-O-(CH_2)_{m6}-COOH$, and from the standpoint of synthesis easiness, more preferably $-NH_2$ or $-O-(CH_2)_{m4}-NH_2$. m4 and m6 each represents an integer of 1 to 5.

$X^2$ and $Y^2$ in formula (29) described above are preferably functional groups different from each other, from the standpoint of synthesizing the branched type hetero monodispersed polyethylene glycol represented by formula (1) described above. As to a preferred combination of $X^2$ and $Y^2$, for example, when $Y^2$ is $-COOH$ or $-O-(CH_2)_{m6}-COOH$, $X^2$ is preferably a hydrogen atom or an amino group containing a divalent saturated hydrocarbon group, and when $Y^2$ is $-NH_2$ or $-O-(CH_2)_{m4}-NH_2$, $X^2$ is preferably a hydrogen atom or a carboxyl group containing a divalent saturated hydrocarbon group.

In formula (29) described above, $L^2$ is a linker responsible for the conjugate between the polyethylene glycol chain and the branch site E and has the same meaning as $L^2$ in formula (1) described above. From the standpoint of raw material purity, $L^2$ in formula (29) described above is preferably an ether bond.

E is a branch site having a divalent bond valence number to $L^2$ and a monovalent bond valence number to $Y^2$, and represents the glycerol site represented by formula (25) described above or formula (26) described above. From the standpoint of raw material purity, E is preferably the branch site represented by formula (25) described above.

Preferred examples of the intermediate for production of the branched type hetero monodispersed polyethylene glycol represented by formula (29) described above include compounds represented by formula (3) described above.

(3)

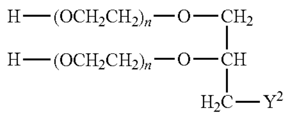

In a method of obtaining the branched type hetero monodispersed polyethylene glycol represented by formula (1) described above using the intermediate for production of the branched type hetero monodispersed polyethylene glycol represented by formula (29) described above, a compound obtained by a known synthesis method can be appropriately used. For example, a method of introducing a maleimide group includes a method in which 3-maleimidopropionic acid or maleimidobutyric acid is reacted with a condensing agent, for example, 1-(3-dimethylaminopropyl)-3-ethylcarbodiimide hydrochloride and then reacted with an amino group of the intermediate for production of the branched type hetero monodispersed polyethylene glycol represented by formula (29) of the invention and a method in which 3-maleimidopropionic acid N-succinimidyl or maleimidobutyric acid N-succinimidyl is reacted with an amino group of the intermediate for production of the branched type hetero monodispersed polyethylene glycol represented by formula (29) of the invention in the presence of a base, for example, triethylamine.

Further, for example, a method for introducing an active ester group includes a method in which N-hydroxysuccinimide is reacted with a carboxyl group of the intermediate for production of the branched type hetero monodispersed polyethylene glycol represented by formula (29) in the presence of a condensing agent, for example, 1-(3-dimethylaminopropyl)-3-ethylcarbodiimide hydrochloride and a method in which disuccinimidyl carbonate is reacted with a hydroxyl group of the intermediate for production of the branched type hetero monodispersed polyethylene glycol represented by formula (29) in the presence of a base, for example, triethylamine.

Moreover, for example, a method for introducing an iodoacetamide group includes, for example, a method in which di(iodoacetic) anhydride or the like is reacted with an amino group of the intermediate for production of the branched type hetero monodispersed polyethylene glycol represented by formula (29) in the presence of a base, for example, triethylamine.

Furthermore, for example, a method for introducing an alkynyl group includes, for example, a method in which propargyl chloroformate, (1R, 8S, 9S)-bicyclo[6.1.0]non-4-yn-9-ylmethyl N-succinimidyl carbonate, dibenzocyclooctyne-N-hydroxysuccinimidyl ester or the like is reacted with an amino group of the intermediate for production of the branched type hetero monodispersed polyethylene glycol represented by formula (29) in the presence of a base, for example, triethylamine.

A typical example of the method of obtaining the branched type hetero monodispersed polyethylene glycol represented by formula (1) described above using the intermediate for production of the branched type hetero monodispersed polyethylene glycol represented by formula (29) described above includes the steps as shown below.

(a) Synthesis of a Compound Having an Active Carbonate Group and a Maleimide Group at Terminals (30)

$$\{H-(OCH_2CH_2)_n-L^2\}_2E-NH_2$$

With an amino group of an intermediate for production of the branched type hetero monodispersed polyethylene glycol represented by formula (30) described above is reacted 3-maleimidopropionic acid N-succinimidyl in the presence of triethylamine in a chloroform solvent to obtain a compound represented by formula (31) shown below.

(31)

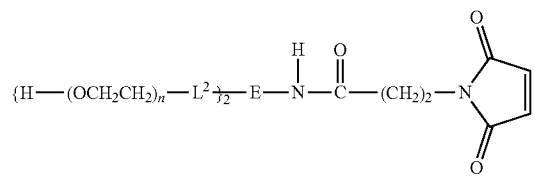

With a hydroxyl group of the compound represented by formula (31) described above is reacted disuccinimidyl carbonate in the presence of triethylamine in a dichloromethane solvent to obtain a branched type hetero monodispersed polyethylene glycol represented by formula (32) shown below. The compound represented by formula (32) is same as a compound represented by formula (1) in which $X^1$ is an active ester group and $Y^1$ is a maleimide group.

(32)

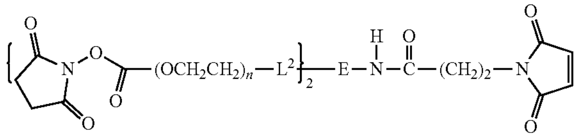

(b) Synthesis of a Compound Having an Active Ester Group and an Iodoacetamide Group at Terminals (33)

$$\{HOOC-(CH_2)_2-(OCH_2CH_2)_n-L^2\}_2-E-NH_2$$

With an amino group of an intermediate for production of the branched type hetero monodispersed polyethylene glycol represented by formula (33) described above is reacted di(iodoacetic)anhydride in the presence of triethylamine in a chloroform solvent to obtain a compound represented by formula (34) shown below.

(34)

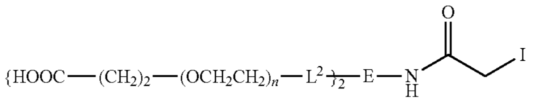

With a carboxyl group of the compound represented by formula (34) described above is reacted N-hydroxysuccinimide in the presence of 1-(3-dimethylaminopropyl)-3-ethylcarbodiimide hydrochloride in a dichloromethane solvent to obtain a branched type hetero monodispersed polyethylene glycol represented by formula (35) shown below. The compound represented by formula (35) is same as a compound represented by formula (1) in which $X^1$ is an active ester group and $Y^1$ is an iodoacetamide group.

(35)

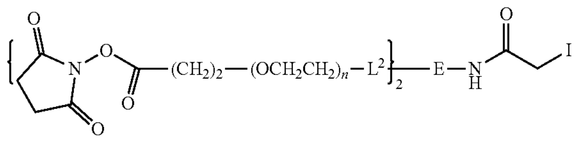

(c) Synthesis of a Compound Having an Alkynyl Group and an Active Ester Group at Terminals (36)

$$\{H_2N-(CH_2)_2-(OCH_2CH_2)_n-L^2\}_2-E-(CH_2)_2-COOH$$

With an amino group of an intermediate for production of the branched type hetero monodispersed polyethylene glycol represented by formula (36) described above is reacted (1R, 8S, 9S)-bicyclo[6.1.0]non-4-yn-9-ylmethyl N-succinimidyl carbonate in the presence of triethylamine in a chloroform solvent to obtain a compound represented by formula (37) shown below.

(37)

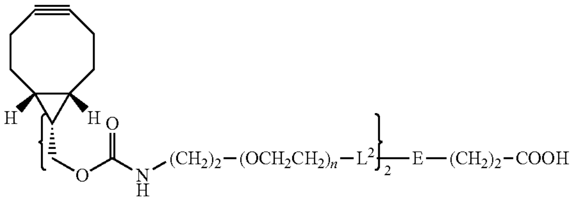

With a carboxyl group of the compound represented by formula (37) described above is reacted N-hydroxysuccinimide in the presence of 1-(3-dimethylaminopropyl)-3-ethylcarbodiimide hydrochloride in a dichloromethane solvent to obtain a branched type hetero monodispersed polyethylene glycol represented by formula (38) shown below. The compound represented by formula (38) is same as a compound represented by formula (1) in which $X^1$ is an alkynyl group and $Y^1$ is an active ester group.

(38)

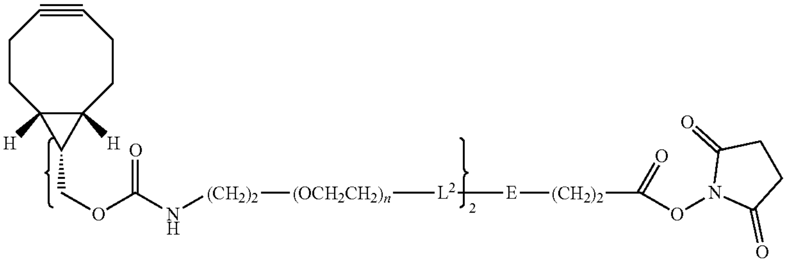

Further, an intermediate for production of the branched type hetero monodispersed polyethylene glycol in the invention is represented by formula (40) shown below.

(40)

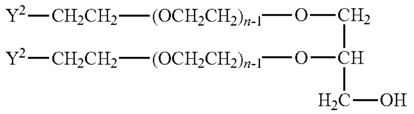

(in formula (40), n represents an integer of 6 to 30. $Y^2$ represents $-NH_2$ or $-O-(CH_2)_{m4}-NH_2$, and m4 represents an integer of 1 to 5.)

[Measurement of Chain Length Purity]

As the chain length purity of the compound represented by formula (1) described above, a chain length purity of the compound represented by formula (3) described above measured by reverse phase chromatography was used. This is because that when the compound represented by formula (1) described above is a compound having an active ester group or an active carbonate group at $X^1$ or $Y^1$, the decomposition thereof occurs during the measurement and the accurate measurement of chain length purity by reverse phase chromatography cannot be carried out. Additionally, since the reaction of obtaining the compound represented by formula (1) described above from the compound represented by formula (3) described above is a condensation reaction between an acid chloride and an acid anhydride, it does not affect to the chain length purity.

[Measurement of Functional Group Purity]

The functional group purity of the compound represented by formula (1) described above is determined based on $^1$H-NMR measurement of functional group purity of the compound represented by formula (3) described above. Similar to the above, this is because that the accurate measurement of functional group purity of the compound represented by formula (1) described above by reverse phase chromatography cannot be carried out. As to the measurement method, first, the functional group purity of the compound represented by formula (3) described above is measured by reverse phase chromatography of the compound represented by formula (3) described above. Next, $^1$H-NMR measurements of the compound represented by formula (1) described above and the compound represented by formula (3) described above are carried out to determine introduction rates of the functional groups $X^1$ and $Y^1$, and the functional group purity is calculated according to formula (F1) shown below:

Functional group purity of the compound represented by formula (1)={(Functional group purity of the compound represented by formula (3)×(Introduction rate of $X^1$)×(Introduction rate of $Y^1$)} (F1)

In the reverse phase chromatography measurement described above, identification of the respective peaks is performed by using a mass spectrometer as a detector, and then the purity is determined from the area values of the respective peaks calculated by using a differential refractometer as a detector. As to the measurement conditions, there is no limitation as long as the respective peaks are separately detected, but when a mass spectrometer is used as a detector, for example, the measurement is carried out under the conditions described below.

Detector: Quattro micro tandem mass spectrometer manufactured by Waters Corp.

Column: TSKgel ODS-80 Ts (particle diameter: 5 μm, column size: 4.6 mm×25 cm) manufactured by Tosoh Corp.

Developing solvent: 5 mM ammonium acetate in methanol/distilled water=j/k j and k represents a volume ratio of methanol and distilled water. j and k are appropriately selected depending on the number of repeating units n of a monodispersed polyethylene glycol and the kind of the terminal functional group of the compound to be measured.

When a differential refractometer is used as a detector, for example, the measurement is carried out under the conditions described below.

Detector: RI-8020 manufactured by Tosoh Corp.

Column: TSKgel ODS-80 Ts (particle diameter: 5 μm, column size: 4.6 mm×25 cm) manufactured by Tosoh Corp.

Developing solvent: 5 mM ammonium acetate in methanol/distilled water=j/k j and k represents a volume ratio of methanol and distilled water and have the same meanings as j and k used in the measurement conditions in the case of using a mass spectrometer as a detector.

In the $^1$H-NMR measurement described above, the introduction rates of the functional groups $X^1$ and $Y^1$ are calculated from the integrated values of the peaks derived from the functional groups $X^1$ and $Y^1$ by using an integrated value of a peak which is not affected by the reaction of obtaining the compound represented by formula (1) described above from the compound represented by formula (3) described above as the standard. The peak used as the standard is appropriately selected depending on the kinds of the functional groups $X^1$ and $Y^1$.

<Method of Producing Intermediate for Production of Branched Type Hetero Monodispersed Polyethylene Glycol>

The intermediate for production of the branched type hetero monodispersed polyethylene glycol of the invention which satisfies the specific conditions described above can be obtained by a method for producing the intermediate for production of the branched type hetero monodispersed polyethylene glycol of the invention. The method for producing the intermediate for production of the branched type hetero monodispersed polyethylene glycol of the invention represented by formula (3) described above is characterized by containing at least step (1), step (2), step (3) and step (4) shown below in this order.

[Step (1)]

The step (1) according to the invention is a step of performing coupling a monodispersed polyethylene glycol derivative represented by formula (4) shown below with a compound represented by formula (5) shown below using any of potassium hydroxide, sodium hydroxide, potassium tert-butoxide and sodium tert-butoxide, as a base catalyst to obtain a compound represented by formula (6) shown below:

$$A-(OCH_2CH_2)_n-B \quad (4)$$

(5)

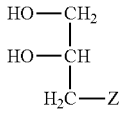

-continued (6)

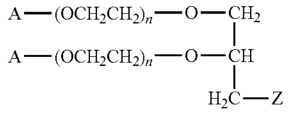

As to the monodispersed polyethylene glycol derivative represented by formula (4) described above, a known method is able to be utilized and a method described in Polym. Chem., 2016, 7, 2389-2394 is effective.

A is a protective group for a hydroxyl group, is not particularly limited as long as it is a protective group stable to the base catalyst used in the coupling described above, and includes, for example, a methoxymethyl group, a benzyloxymethyl group, a 2-methoxyethoxymethyl group, a tetrahydropyranyl group, an allyl group, a benzyl group, a 4-methoxybenzyl group, a trimethylbenzyl group, a triphenylmethyl group, a triethylsilyl group, a triisopropylsilyl group, a tert-butyldimethylsilyl group and a tert-butyldiphenylsilyl group. From the standpoint of synthesis easiness, A is preferably a benzyloxymethyl group, a tetrahydropyranyl group, a benzyl group, a trimethylbenzyl group or a triphenylmethyl group, and more preferably a benzyl group or a triphenylmethyl group.

B is a leaving group, is not particularly limited as long as it is a leaving group having reactivity in the coupling described above, and includes, for example, a chloro group, a bromo group, an iodo group, a mesylate group, a tosylate group, a chloromethanesulfonate group and a trifluoromethanesulfonate group. From the standpoint of synthesis easiness, B is preferably a bromo group, a mesylate group, a tosylate group or a chloromethanesulfonate group, and more preferably a mesylate group.

n represents a number of repeating units of a monodispersed polyethylene glycol and is an integer of 6 to 30. From the standpoint of using as a linker for ADC, n is preferably an integer of 6 to 24.

The compound represented by formula (5) described above is able to be synthesized from commercially available 2,2-dimethyl-1,3-dioxolane-4-methanol by appropriately utilizing a known method.

In the compound represented by formula (5) described above, Z represents $—Z^1$ or $—O—(CH_2)_{m5}—Z^1$. m5 represents an integer of 1 to 5. From the standpoint of synthesis easiness, Z is preferably any of $—Z^1$, $—O—(CH_2)_2—Z^1$, $—O—(CH_2)_3\text{-}Z^1$ and $—O—(CH_2)_5\text{-}Z^1$. $Z^1$ is not particularly limited as long as it is a functional group stable to the base catalyst used in the coupling described above. From the standpoint of producing the intermediate for production of the branched type hetero monodispersed polyethylene glycol represented by formula (4) described above, $Z^1$ is preferably an atomic group containing a nitrogen atom capable of being converted to an amino group, and is preferably, for example, a protected form of an amino group, an azide group or a cyano group.

Further, the protected form of an amino group means a conjugate of an amino group and a protective group. The protective group is not particularly limited as long as it is a protective group stable to the base catalyst used in the coupling described above and includes, for example, a 9-fluorenylmethylcarbonyl group, a tert-butoxycarbonyl group, a benzyloxycarbonyl group and a dibenzyl group, preferably a tert-butoxycarbonyl group, a benzyloxycarbonyl group and a dibenzyl group.

The combination of the protective group A in formula (4) described above and $Z^1$ in formula (5) described above is not particularly limited as long as $Z^1$ is stable to deprotection conditions of the protective group A in the step (2). In the case where the deprotection in the step (2) is a hydrolysis reaction under an acidic condition, $Z^1$ is preferably a protected form of an amino group with a 9-fluorenylmethylcarbonyl group, a protected form of an amino group with a tert-butoxycarbonyl group, a protected form of an amino group with a benzyloxycarbonyl group, a protected form of an amino group with a dibenzyl group, an azide group or a cyano group. In the case where the deprotection in the step (2) is a catalytic hydrogenation, $Z^1$ is preferably a protected form of an amino group with a 9-fluorenylmethylcarbonyl group or a protected form of an amino group with a tert-butoxycarbonyl group.

The base catalyst used in the coupling described above is not particularly limited as long as it is a base catalyst which proceeds the reaction. It is preferably abase catalyst having a pKa in an aqueous solution of 15 to 20 and includes, for example, potassium hydroxide (pKa=15.7), sodium hydroxide (pKa=15.7), potassium tert-butoxide (pKa=19), sodium tert-butoxide (pKa=15.7), sodium methoxide (pKa=15.5) and sodium ethoxide (pKa=16). More preferably, it includes potassium hydroxide, sodium hydroxide, potassium tert-butoxide and sodium tert-butoxide. In the case of using a base catalyst having a pKa in an aqueous solution exceeding 20, for example, sodium hydride, etc., the branch site represented by formula (5) described above is decomposed by a reaction with the base catalyst so that the yield in the coupling and the purity are decreased. On the other hand, in the case of using a base catalyst having a pKa in an aqueous solution less than 15, for example, trimethylamine, etc., the progress of the coupling described above tends to be slow. Further, the use amount of the base catalyst described above has no problem as long as the reaction proceeds and is ordinarily from 2.0 to 10 times, preferably from 2.1 to 5 times in a molar ratio, with respect to the compound represented by formula (5) described above. In the case where the use amount of the base catalyst described above is less than the lower limit described above, the reaction does not proceeds completely and the hydroxyl group of the compound represented by formula (5) described above tends to remain without introduction of a monodispersed polyethylene glycol chain to the hydroxyl group. On the other hand, in the case where the use amount exceeds the upper limit described above, due to the excessive base a side reaction is liable to proceed.

As to the coupling described above, the reaction can be performed in a solvent. The solvent described above is not particularly limited as long as it does not react with the compound represented by formula (4) described above and the compound represented by formula (5) described above and includes, for example, an aprotic polar solvent, for example, tetrahydrofuran, acetonitrile, DMF, dichloromethane or chloroform and a mixture thereof. The use amount of the solvent described above is ordinarily from 1 to 100 times, preferably from 2 to 50 times, most preferably from 3 to 30 times in a mass ratio, with respect to the compound represented by formula (4) described above. In the case where the use amount of the solvent described above exceeds the upper limit described above, the progress of the coupling described above tends to be slow.

The reaction temperature of the coupling described above vary depending on the solvent used or the like and is ordinarily from 0 to 100° C. In the case where the reaction temperature described above is less than the lower limit described above, the progress of the reaction is liable to be slow. On the other hand, in the case where the reaction temperature exceeds the upper limit described above, due to the excessive temperature a side reaction is liable to proceed. Further, the reaction time of the coupling described above vary depending on the conditions, for example, the reaction temperature described above or the like and is usually preferably approximately from 1 to 48 hours.

The use amount of the compound represented by formula (4) described above in the coupling described above is ordinarily from 2.0 to 10 times, preferably from 2.1 to 4 times in a molar ratio, with respect to the compound represented by formula (5) described above. In the case where the use amount of the compound represented by formula (4) described above is less than the lower limit described above, the reaction does not proceeds completely and the hydroxyl group of the compound represented by formula (5) described above tends to remain without introduction of a monodispersed polyethylene glycol chain to the hydroxyl group. On the other hand, in the case where the use amount exceeds the upper limit, the excess of the compound represented by formula (4) described above is of no use and not only the production cost increases but also the yield decreases because it is difficult to separate the excess of the compound represented by formula (4) described above from the compound represented by formula (6) described above which is the reaction product.

In the step (1), the compound represented by formula (6) described above can be obtained by the coupling as described above. The compound described above may be used as it is without purification in the next step (2) or may be used after purification with silica gel column chromatography, an adsorbent treatment or the like. In the invention, however, the hetero type monodispersed polyethylene glycol of the invention of high purity can be obtained without performing purification with silica gel column chromatography.

[Step (2)]

The step (2) according to the invention is a step of deprotecting the protective group A of the compound represented by formula (6) described above to obtain a compound represented by formula (7) shown below.

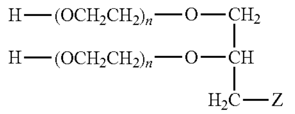

(7)

In formula (7) described above, Z represents $—Z^1$ or $—O—(CH_2)_{m5}—Z^1$, and $Z^1$ represents any of a protected form of an amino group, an azide group and a cyano group. m5 represents an integer of 1 to 5. n represents an integer of 6 to 30. The protected form of an amino group described above is derived from $Z^1$ in the compound represented by formula (6) described above and has the same meaning as $Z^1$ in formula (6) described above.

A method for deprotecting the protective group A of the compound represented by formula (6) described above vary depending on the kind of the protective group and includes a method of performing deprotection utilizing a known method. For example, in the case where A is an ether-based protective group, for example, a methoxymethyl group, a tetrahydropyranyl group or a trityl group, the deprotection includes a method by hydrolysis under an acidic condition. Further, for example, in the case where A is a protective group containing a benzyl group, for example, a benzyl group or a trityl group, the deprotection includes a method by catalytic hydrogenation in the presence of a catalyst. Moreover, for example, in the case where A is a silyl-based protective group, for example, a triethylsilyl group, the deprotection includes a desilylation reaction by a fluoride ion, for example, tetrabutylammonium fluoride.

In the case where the deprotection described above is hydrolysis, the hydrolysis can be performed in a solvent. The solvent described above includes, for example, a protic polar solvent, for example, water, methanol or ethanol and a mixture thereof. Further, the solvent may contain an organic solvent miscible with water in any ratio, for example, tetrahydrofuran, acetone or DMF. The use amount of the solvent described above is ordinarily from 1 to 100 times, preferably from 2 to 50 times, most preferably from 3 to 30 times in a mass ratio, with respect to the compound represented by formula (6) described above. In the case where the use amount of the solvent described above exceeds the upper limit described above, the progress of the hydrolysis described above tends to be slow. As to the hydrolysis described above, the reaction is performed by using an acid catalyst. The acid catalyst described above includes, for example, an inorganic acid, for example, hydrochloric acid, sulfuric acid or phosphoric acid, an organic acid, for example, p-toluenesulfonic acid monohydrate or methanesulfonic acid, and a cation exchange resin, for example, Amberlyst. The equivalent of the acid catalyst described above is ordinarily from 0.1 to 2 times, preferably from 0.2 to 1 time in a molar ratio, with respect to the compound represented by formula (6) described above. The reaction temperature of hydrolysis described above vary depending on the solvent used or the like and is ordinarily from 0 to 100° C. In the case where the reaction temperature described above is less than the lower limit described above, the progress of the reaction is liable to be slow. On the other hand, in the case where the reaction temperature exceeds the upper limit described above, due to the excessive temperature a side reaction is liable to proceed. Further, the reaction time of the hydrolysis described above vary depending on the conditions, for example, the reaction temperature described above or the like and is usually preferably approximately from 1 to 48 hours.

In the case where the deprotection described above is catalytic hydrogenation, the reaction is performed in the presence of a catalyst. The catalyst described above includes, for example, palladium carbon or palladium hydroxide carbon. The equivalent of the catalyst described above is ordinarily from 0.01 to 1 time, preferably from 0.05 to 0.2 times in a weight ratio, with respect to the compound represented by formula (6) described above. As to the catalytic hydrogenation described above, the reaction can be performed in a solvent. The solvent described above includes, for example, water, methanol, ethanol, tetrahydrofuran, ethyl acetate, DMF and a mixture thereof. The use amount of the solvent described above is ordinarily from 1 to 100 times, preferably from 2 to 50 times, most preferably from 3 to 30 times in a mass ratio, with respect to the compound represented by formula (6) described above. In the case where the use amount of the solvent described above exceeds the upper limit described above, the progress of the catalytic hydrogenation described above tends to be slow. The reaction temperature of the catalytic hydrogenation described above vary depending on the solvent used or the like and is ordinarily from 0 to 100° C. In the case where the reaction temperature described above is less than the lower limit described above, the progress of the reaction is liable to be slow. On the other hand, in the case where the reaction temperature exceeds the upper limit described above, due to the excessive temperature a side reaction is liable to proceed. Further, the reaction time of the hydrolysis described above vary depending on the conditions, for example, the reaction temperature described above or the like and is usually preferably approximately from 1 to 48 hours.

In the case where the deprotection described above is a desilylation reaction, it includes deprotection by acid hydrolysis and deprotection by a fluoride ion. The deprotection by acid hydrolysis can be performed by the method same as in the deprotection by the hydrolysis of the ether-based protective group described above. The deprotection by a fluoride ion is performed by using a reagent having a fluoride ion, for example, tetrabutylammonium fluoride or hydrogen fluoride. The equivalent of the reagent having a fluoride ion described above is ordinarily from 1.0 to 2 times, preferably from 1.1 to 1.5 times in a molar ratio, with respect to the compound represented by formula (6) described above. As to the deprotection by a fluoride ion described above, the reaction can be performed in a solvent. The solvent described above includes, for example, water, methanol, ethanol, tetrahydrofuran, ethyl acetate, DMF and a mixture thereof. The use amount of the solvent described above is ordinarily from 1 to 100 times, preferably from 2 to 50 times, most preferably from 3 to 30 times in a mass ratio, with respect to the compound represented by formula (6) described above. In the case where the use amount of the solvent described above exceeds the upper limit described above, the progress of the catalytic hydrogenation described above tends to be slow. The reaction temperature of the deprotection by a fluoride ion described above vary depending on the solvent used or the like and is ordinarily from 0 to 100° C. In the case where the reaction temperature described above is less than the lower limit described above, the progress of the reaction is liable to be slow. On the other hand, in the case where the reaction temperature exceeds the upper limit described above, due to the excessive temperature a side reaction is liable to proceed. Further, the reaction time of the catalytic hydrogenation described above vary depending on the conditions, for example, the reaction temperature described above or the like and is usually preferably approximately from 1 to 48 hours.

In the step (2), the compound represented by formula (7) described above can be obtained by the deprotection as described above. The compound described above may be used as it is without purification in the next step (3) or may be used after purification with silica gel column chromatography, an adsorbent treatment or the like. In the invention, however, the hetero type monodispersed polyethylene glycol of the invention of high purity can be obtained without performing purification with silica gel column chromatography.

[Step (3)]

The step (3) according to the invention is a step of subjecting a reaction product containing the compound represented by formula (7) described above to separatory purification.

For example, the compound represented by formula (4) described above excessively added in the step (1) described above remains in the compound represented by formula (6) described above which is the reaction product. The protective group A of the compound represented by formula (4) described above is deprotected in the step (2) same as the compound represented by formula (6) described above to form a compound represented by formula (39) shown below.

$$H—(OCH_2CH_2)_n—B \quad (39)$$

In formula (39) described above, B is a leaving group, and n represents a number of repeating units of a monodispersed polyethylene glycol and is an integer of 6 to 30. The leaving group described above is derived from B in the compound represented by formula (4) described above and has the same meaning as B in formula (4) described above.

The step (3) described above is a step of separatory washing the compound represented by formula (39) described above contained in the desired compound represented by formula (7) described above dissolved in an organic solvent with an aqueous solution.

The organic solvent used in the step (3) described above includes, for example, ethyl acetate, toluene, chloroform or dichloromethane and is preferably chloroform or dichloromethane from the standpoint of solubility of the desired compound. The use amount of the organic solvent described above is ordinarily from 2 to 30 times, preferably from 3 to 20 times in a mass ratio, with respect to the reaction product containing the compound represented by formula (7) described above and the compound represented by formula (39) described above. In the case where the use amount of the organic solvent described above is less than the lower limit described above, the compound represented by formula (7) described above is liable to be dissolved in an aqueous solution. On the other hand, in the case where the use amount exceeds the upper limit described above, washing efficiency of the compound represented by formula (39) described above tends to decrease.

The aqueous solution used in the step (3) described above is not particularly limited as long as it is able to dissolve the compound represented by formula (39) described above and includes, for example, ion-exchanged water and an aqueous solution with low salt concentration of sodium chloride, potassium chloride or the like. The use amount of the aqueous solution described above is ordinarily from 2 to 30 times, preferably from 3 to 20 times in a mass ratio, with respect to the reaction product containing the compound represented by formula (7) described above and the compound represented by formula (39) described above. In the case where the use amount of the aqueous solution described above is less than the lower limit described above, washing efficiency of the compound represented by formula (39) described above decrease. On the other hand, in the case where the use amount exceeds the upper limit described above, the compound represented by formula (7) described above is liable to be dissolved in an aqueous phase.

In the step (3) described above, a ratio of the organic solvent described above and the aqueous solution described above is ordinarily from 0.2 to 3.0, preferably from 0.5 to 2.0 in a mass ratio as a value of organic solvent/aqueous solution.

The temperature of the step C described above varies depending on n. In the case where n is from 6 to 10, the temperature described above is preferably from 1 to 25° C., and more preferably from 5 to 20° C. In the case where n is from 11 to 30, the temperature described above is preferably from 1 to 15° C., and more preferably from 5 to 10° C. In the case where the temperature described above exceeds the upper limit described above, the compound represented by formula (39) described above cannot be removed because it is dissolved in the organic phase. Further, the number of times of performing the separatory washing described above is not particularly limited and it is preferred to perform several times while confirming the compound represented by formula (39) described above contained in the organic solvent by TLC, MS measurement or the like.

[Step (4)]

The step (4) according to the invention is a step of subjecting the compound represented by formula (7) described above to a deprotection treatment or a reduction treatment to obtain the intermediate for production of the branched type hetero monodispersed polyethylene glycol represented by formula (3) described above.

The treatment used in the step (4) described above vary depending on the kind of $Z^1$ in the compound represented by formula (39) described above and it can be performed appropriately by a known method depending on the kind of $Z^1$. For example, in the case where $Z^1$ is a protected form of an amino group, the treatment used in the step (4) described above is a deprotection treatment. The deprotection treatment described above vary depending on the kind of protective group in the protected form of an amino group described above and in the case where the protective group is a 9-fluorenylmethylcarbonyl group, the deprotection includes a reaction using a secondary amine, for example, piperidine or pyrrolidine. In the case where the protective group is a tert-butoxycarbonyl group, the deprotection includes a reaction using trifluoroacetic acid, 4N hydrochloric acid or the like. In the case where the protective group is a benzyloxycarbonyl group, the deprotection includes catalytic hydrogenation in the presence of a palladium carbon catalyst. For example, in the case where $Z^1$ is an azide group or a cyano group, the treatment used in the step (4) described above is a reduction treatment. The reduction treatment described above vary depending on the kind of $Z^1$ and in the case where $Z^1$ is an azide group, the reduction includes Staudinger reduction using triphenylphosphine as a reducing agent and catalytic hydrogenation in the presence of a palladium carbon catalyst. In the case where $Z^1$ is a cyano group, the reduction includes hydrogenation in the presence of a palladium carbon catalyst or a nickel catalyst and the like.

In the reaction product described above, since the impurity is able to be removed by the separatory purification treatment in the step (3) described above, purification by silica gel column chromatography or the like is not needed. Additionally, the intermediate for production of the branched type hetero monodispersed polyethylene glycol containing the compound represented by formula (3) described above obtained is able to use as it is in the production of the branched type hetero monodispersed polyethylene glycol of the invention described above, but it may be used after purification by treatment, for example, crystallization, adsorbent treatment or silica gel column chromatography.

According to the production method described above, the intermediate for production of the branched type hetero monodispersed polyethylene glycol represented by formula (3) described above can be obtained. Since the intermediate for production of the branched type hetero monodispersed polyethylene glycol represented by formula (3) described above of the invention has high chain length purity and high functional group purity, the branched type hetero monodispersed polyethylene glycol represented by formula (1) described above or formula (2) described above can be obtained in high chain length purity and high functional group purity without performing purification by treatment, for example, silica gel column chromatography.

The chain length purity and functional group purity of the intermediate for production of the branched type hetero monodispersed polyethylene glycol represented by formula (3) described above can be determined by reverse phase chromatography measurement.

In the case where $L^3$ in the compound represented by formula (1) is a single bond, the compound can be obtained by reacting disuccinimidyl carbonate with a hydroxyl group of the compound represented by formula (40) in the presence of triethylamine in dichloromethane solvent.

The method for producing the intermediate for production of the branched type hetero monodispersed polyethylene glycol represented by formula (40) described above is characterized by containing at least step (1') to step (4') shown below in this order.

[Step (1')]

The step (1') includes performing coupling a monodispersed polyethylene glycol derivative represented by formula (41) shown below with a compound represented by formula (42) shown below using a base catalyst having a pKa in an aqueous solution of 15 to 20 to obtain a compound represented by formula (43) shown below.

$$Z—CH_2CH_2—(OCH_2CH_2)_{n-1}—B \quad (41)$$

(in formula (41), Z represents $—Z^1$ or $—O—(CH_2)_{m5}—Z^1$, $Z^1$ represents any of a protected form of an amino group, an azide group and a cyano group, m5 represents an integer of 1 to 5, B represents a leaving group, and n represents an integer of 6 to 30.), (42)

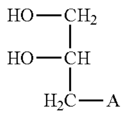

(in formula (42), A represents a protective group for a hydroxyl group.), (43)

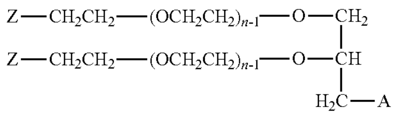

(in formula (43), A represents a protective group for a hydroxyl group, Z represents $—Z^1$ or $—O—(CH_2)_{m5}—Z^1$, $Z^1$ represents any of a protected form of an amino group, an azide group and a cyano group, m5 represents an integer of 1 to 5, and n represents an integer of 6 to 30.)

[Step (2')]

The step (2') includes deprotecting the protective group A of the compound represented by formula (43) described above to obtain a compound represented by formula (44) shown below.

(44)

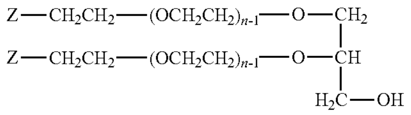

(in formula (44), Z represents $—Z^1$ or $—O—(CH_2)_{m5}—Z^1$, $Z^1$ represents any of a protected form of an amino group, an azide group and a cyano group, m5 represents an integer of 1 to 5, and n represents an integer of 6 to 30.)

[Step (3')]

The step (3') includes subjecting the compound represented by formula (44) described above to deprotection treatment or reduction treatment to obtain the intermediate for production of the branched type hetero monodispersed polyethylene glycol represented by formula (40) described above.

[Step (4')]

The step (4') includes subjecting the compound represented by formula (40) described above to separatory purification.

The base catalyst described above is preferably any of potassium hydroxide, sodium hydroxide, potassium tert-butoxide and sodium tert-butoxide.

The chain length purity and functional group purity of the intermediate for production of the branched type hetero monodispersed polyethylene glycol represented by formula (40) described above can be determined by reverse phase chromatography measurement.

<Branched Type Hetero Monodispersed Polyethylene Glycol Conjugate>

By using the branched type hetero monodispersed polyethylene glycol represented by formula (1) or formula (2) described above of the invention, the hetero type monodispersed polyethylene glycol conjugate in which the compound (hetero type polyethylene glycol) and a biofunctional molecule are conjugated can be obtained.

The biofunctional molecule described above includes protein drug, polypeptide, enzyme, antibody, antibody drug, gene, nucleic acid compound containing oligonucleic acid or the like, nucleic acid drug, anticancer drug, and other drugs, for example, low molecular weight drug.

The method for obtaining the hetero type monodispersed polyethylene glycol conjugate described above includes, for example, a method wherein first, a drug, for example, an anticancer drug or a protein drug is introduced into $X^1$ of the compound represented by formula (1) described above or formula (2) described above, and an antibody is conjugated to the another terminal $Y^1$. Since the compound represented by formula (1) described above or formula (2) described above has functional groups different from each other at the both terminals thereof in high purity, when it is used as ADC, generation of a compound losing either the desired antibody or the desired drug is suppressed so that the increase in the effect of ADC is expected.

EXAMPLE

The invention will be described more specifically with reference to the examples, but the invention should not be construed as being limited thereto.

In each synthesis example, JMTC-400 manufactured by JEOL Ltd. was used for measurement of nuclear magnetic resonance ($^1$H-NMR) and Quattro micro tandem mass spectrometer manufactured by Waters Corp. was used for measurement of mass spectrometry (ESI-MS).

Example 1-1

Synthesis of Compound 4 Represented by Formula (5) Wherein $Z^1$ is Azide Group

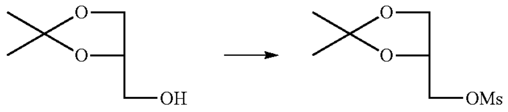

1 2

(in the formula, Ms represents a methanesulfonyl group.)

Compound 1 (20.0 g, 0.151 mol) and toluene (200 mL) were charged in an eggplant-shaped flask, the inside of the eggplant-shaped flask was purged with nitrogen, and triethylamine (18.4 g, 0.182 mol) was added thereto. Methanesulfonyl chloride (19.1 g, 0.167 mol) was dropwise added thereto at 0° C., and the mixture was stirred at room temperature for 2 hours. After 2 hours, the disappearance of Compound 1 was confirmed by ESI-MS measurement, and 150 mL of 1M hydrochloric acid was added thereto to cause liquid separation. The organic phase was washed once with 150 mL of 1M hydrochloric acid, twice with 150 mL of an aqueous saturated sodium bicarbonate solution and once with 150 mL of an aqueous saturated sodium chloride solution. Sodium sulfate was added to the organic phase to dry, followed by filtration. The filtrate was concentrated under a reduced pressure to obtain Compound 2 as pale yellow colored transparent liquid.

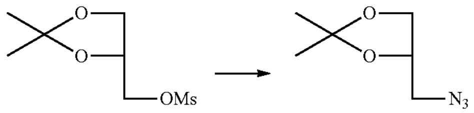

2 3

(in the formula, Ms represents a methanesulfonyl group.)

Compound 2 (20.8 g, 0.099 mol) and N,N'-dimethylformamide (100 mL) were charged in an eggplant-shaped flask, sodium azide (7.72 g, 0.119 mol) was added thereto, and the mixture was stirred at 100° C. for 5 hours. After 5 hours, the disappearance of Compound 2 was confirmed by $^1$H-NMR measurement, and the mixture was diluted with 150 mL of ethyl acetate. The resulting solution was washed once with 100 mL of an aqueous saturated sodium chloride solution and twice with 60 mL of an aqueous saturated sodium chloride solution. Further, 100 mL of ethyl acetate was added the aqueous saturated sodium chloride solution used at the first time to extract, and the organic phase was washed twice with 50 mL of an aqueous saturated sodium chloride solution. The two organic phases were put together, and sodium sulfate was added thereto to dry, followed by filtration. The filtrate was concentrated under a reduced pressure to obtain Compound 3 as pale yellow colored transparent liquid.

Yield: 15.3 g

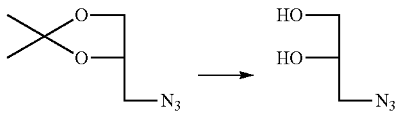

3 4

Compound 3 (13.3 g, mol), tetrahydrofuran (5 mL) and 1M hydrochloric acid (10 mL) were charged in an eggplant-shaped flask, and the mixture was stirred at room temperature for 5 hours. After 5 hours, the disappearance of Compound 3 was confirmed by ESI-MS measurement, and the reaction solution was concentrated under a reduced pressure (only tetrahydrofuran). Ethyl acetate (50 mL) was added to the residue to cause liquid separation, and the organic phase was washed three times with 30 mL of an aqueous saturated sodium chloride solution. Sodium sulfate was added to the organic phase to dry, followed by filtration. The filtrate was concentrated under a reduced pressure to obtain Compound 4 as pale yellow colored transparent liquid.

Yield: 2.01 g

MS ($ESI^+$): Compound 4 118.1 $[M+H]^+$ $^1$H-NMR ($CDCl_3$, 400 MHz): 3.89 (m, 1H), 3.71 (dd, 1H), 3.61 (dd, 1H), 3.41 (m, 2H)

Example 1-2

Synthesis of Compound 9 Represented by Formula (3) Wherein $Y^2$ is —$NH_2$ and n is 12

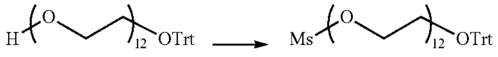

5 6

(in the formula, Trt represents a triphenylmethyl group.)

Compound 5 (50.0 g, 63.4 mmol) of Compound 5 obtained by a method described in Polym. Chem., 2016, 7, 2389-2394 and toluene (250 mL) were charged in an eggplant-shaped flask. The inside of the eggplant-shaped flask was purged with nitrogen, and triethylamine (10.5 mL, 76.1 mmol) was added thereto. Methanesulfonyl chloride (5.4 mL, 69.8 mol) was added dropwise thereto at 0° C. and the mixture was stirred at room temperature for 2 hours. After 2 hours, the disappearance of Compound 5 was confirmed by ESI-MS measurement, and 100 mL of 1M hydrochloric acid was added thereto to cause liquid separation. The organic phase was washed once with 100 mL of 1M hydrochloric acid, twice with 100 mL of an aqueous saturated sodium bicarbonate solution and once with 100 mL of an aqueous saturated sodium chloride solution. Sodium sulfate was added to the organic phase to dry, followed by filtration. The filtrate was concentrated under a reduced pressure to obtain Compound 6 as pale yellow colored transparent liquid.

Yield: 52.0 g

[Step (1)]

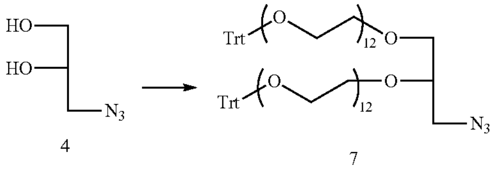

4 7

(in the formula, Trt represents a triphenylmethyl group.)

Compound 4 (1.64 g, 14.0 mmol) and Compound 6 (36.4 g, 42.0 mmol) were charged in an eggplant-shaped flask and subjected to toluene azeotrope (30 mL×2). Tetrahydrofuran (270 mL) was added thereto, and the inside of the eggplant-shaped flask was purged with nitrogen. Potassium hydroxide (powder, 2.36 g, 42 mmol) was added thereto and the mixture was stirred under reflux with heating for 7 hours. After 7 hours, the disappearance of Compound 4 was confirmed by ESI-MS measurement, and 10 mL of an aqueous saturated ammonium chloride solution was added thereto to quench the reaction. The solution was concentrated under a reduced pressure (only tetrahydrofuran), and the residue was dissolved in 150 mL of toluene. The solution was washed twice with 100 mL of ion-exchanged water, once with 100 mL of an aqueous saturated sodium bicarbonate solution and once with 100 mL of an aqueous saturated sodium chloride solution. Sodium sulfate was added to the organic phase to dry, followed by filtration. The filtrate was concentrated under a reduced pressure to obtain Compound 7 as pale yellow colored transparent liquid.

Yield: 35.5 g

[Steps (2) to (3)]

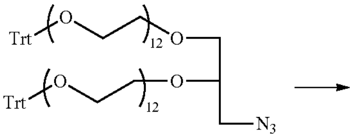

7

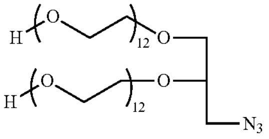

8

(in the formula, Trt represents a triphenylmethyl group.)

Compound 7 (35.5 g) and methanol (180 mL) were charged in an eggplant-shaped flask. P-Toluenesulfonic acid monohydrate (3.99 g, 21.0 mmol) and hexane (150 mL) were added thereto, and the mixture was stirred at room temperature for 30 minutes. After 30 minutes, the hexane layer was removed, and then hexane (150 mL) was added thereto, and the mixture was stirred at room temperature for 30 minutes. After the same operation was performed four times, the disappearance of Compound 7 was confirmed by ESI-MS measurement, and 120 mL of an aqueous saturated sodium bicarbonate solution was added thereto. The mixed solution was washed twice with 150 ml of hexane. The solution of the product was concentrated under a reduced pressure, 180 ml of dichloromethane was added to the residue, and the mixture was washed three times with 180 mL of ion-exchanged water and once with 180 mL of an aqueous saturated sodium chloride solution (10° C.). Sodium sulfate was added to the organic phase to dry, followed by filtration. The filtrate was concentrated under a reduced pressure to obtain Compound 8 as a brown colored solid.

Yield: 11.5 g

[Step (4)]

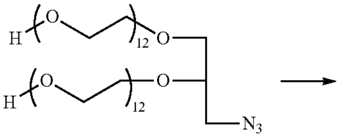

8

-continued

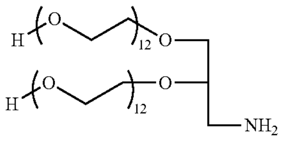

9

Compound 8 (11.5 g) and methanol (60 mL) were charged in an eggplant-shaped flask, and the inside of the eggplant-shaped flask was purged with nitrogen. Palladium carbon (1.2 g) was added thereto, and the inside of the eggplant-shaped flask was purged with hydrogen, followed by stirring at room temperature for 5 hours. After 5 hours, the disappearance of Compound 8 was confirmed by ESI-MS measurement, and the reaction solution was filtered (glass fiber filter paper). The filtrate was concentrated under a reduce pressure, and the residue was dissolved in 60 mL of dichloromethane. The solution was extracted once with 60 mL of 1M hydrochloric acid and washed twice with 60 mL of dichloromethane. Sodium chloride was added to the aqueous phase to be saturated and extracted three times with 60 mL of dichloromethane. The organic phases were put together, and sodium sulfate was added thereto to dry, followed by filtration. The filtrate was concentrated under a reduced pressure to obtain Compound 9 as pale yellow colored transparent liquid. The molar yield of three steps based on Compound 4 was 51.0%. The results were summarized in Table 1.

Yield: 9.6 g

MS ($ESI^+$): Compound 9 1148.2 $[M+H]^+$ $^1$H-NMR ($CDCl_3$, 400 MHz): 3.62 (m, 99H), 3.16 (dd, 1H), 3.04 (dd, 1H))

Example 1-3

Synthesis of Compound 11 Represented by Formula (1) Wherein $X^1$ is Active Carbonate Group, $Y^1$ is Maleimide Group. $L^2$ is Ether Bond, $L^3$ is $—NHC(O)—(CH_2)_2—$ and n is 12

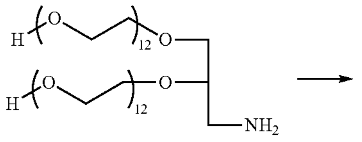

9

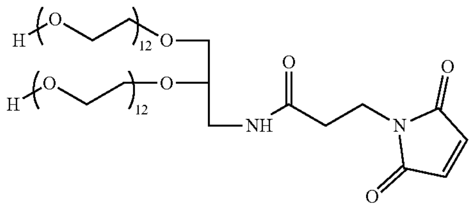

10

3-maleimidopropionic acid N-succinimidyl (301 mg, 1.1 mmol), dibutylhydroxytoluene (4 mg, 0.018 mmol) and chloroform (30 mL) were charged in an eggplant-shaped flask. Compound 9 (1.0 g, 0.87 mmol) and triethylamine (0.17 mL, 1.2 mmol) were dissolved in chloroform (20 mL) and the solution was dropwise added to the flask at room temperature. After stirring at room temperature for 4 hours, the disappearance of Compound 9 was confirmed by ESI-MS measurement, and 50 mL of an aqueous saturated sodium chloride solution (pH=2.0) was added thereto to cause liquid separation. The organic phase was washed with 50 mL of an aqueous saturated sodium chloride solution (pH=2.0) and concentrated under a reduced pressure. 50 mL of citric acid buffer (pH=3.0) was added to the residue and the mixture was washed three times with 50 mL of toluene-chloroform (10:3 w/w). The aqueous phase was extracted three times with 50 mL of chloroform. The organic phases were put together, and magnesium sulfate was added thereto to dry, followed by filtration. The filtrate was concentrated under a reduced pressure to obtain Compound 10 as a white solid.

Yield: 928 mg

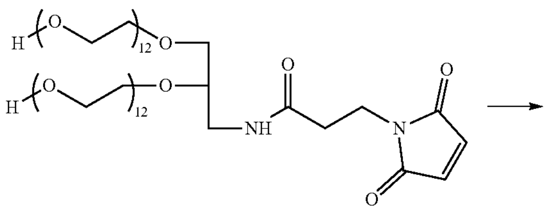

10

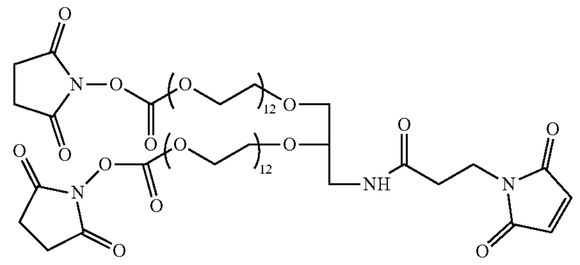

11

Compound 10 (928 mg, 0.71 mmol), triethylamine (0.32 mL, 2.3 mmol), dibutylhydroxytoluene (3 mg, 0.014 mmol) and dichloromethane (45 mL) were charged in an eggplant-shaped flask. Disuccinimidyl carbonate (538 mg, 2.1 mmol) was added thereto and the mixture was stirred at room temperature for 5 hours. After 5 hours, the disappearance of Compound 10 was confirmed by ESI-MS measurement, 45 mL of an aqueous sodium chloride solution (pH=2.0) was added thereto to cause liquid separation. The organic phase was washed with 45 mL of an aqueous sodium chloride solution (pH=2.0) and concentrated under a reduced pressure. 45 mL of 1M hydrochloric acid was added to the residue, the mixture was washed twice with 45 mL of ethyl acetate, and the aqueous phase was extracted twice with 45 mL of dichloromethane. The organic phases were put together, washed twice with 45 mL of an aqueous 20% sodium chloride solution, then the organic phases were put together, and magnesium sulfate was added thereto to dry, followed by filtration. The filtrate was concentrated under a reduced pressure to obtain Compound 11 as a white solid.

Yield: 994 mg

MS ($ESI^+$): Compound 11 1598.7 $[M+NH_4]^+$ $^1$H-NMR ($CD_3OD$, 400 MHz): 6.83 (s, 2H), 4.47 (m, 4H), 3.62 (m, 97H), 3.38 (dd, 1H), 3.18 (dd, 1H), 2.83 (s, 8H), 2.49 (t, 2H)

Example 2-1

Synthesis of Compound 15 Represented by Formula (5) Wherein $Z^1$ is Protected Form of Amino Group and m5 is 3

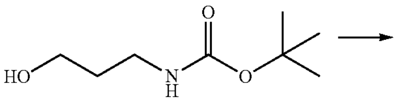

12

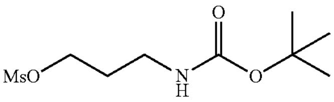

13

3-Bocamino-1-propanol 12 (5.0 g, 28.5 mmol) and toluene (25 mL) were charged in a two-necked eggplant-shaped flask, the inside of the eggplant-shaped flask was purged with nitrogen, and triethylamine (5.14 mL, 37.1 mmol) was added thereto. Methanesulfonyl chloride (2.43 mL, 31.4 mmol) was dropwise added thereto at 0° C., and the mixture was stirred at room temperature for 2 hours. After 2 hours, the disappearance of Compound 12 was confirmed by ESI-MS measurement, and 25 mL of 1M hydrochloric acid was added thereto to cause liquid separation. The organic phase was washed once with 25 mL of an aqueous saturated sodium bicarbonate solution and once with 25 mL of an aqueous saturated sodium chloride solution. 3 g of sodium sulfate was added to the organic phase to dry, followed by filtration. The filtrate was concentrated under a reduced pressure to obtain Compound 13 as pale yellow colored transparent liquid.

Yield: 6.9 g

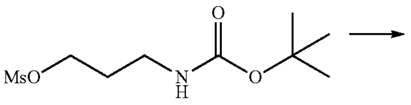

13

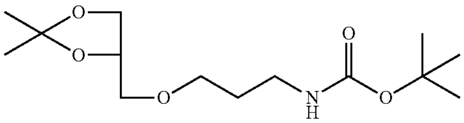

14

(in the formula, Ms represents a methanesulfonyl group.)

Sodium hydride (1.5 g) was charged in a four-necked eggplant-shaped flask, followed by nitrogen purge. Washing with 10 mL of hexane was performed twice, 30 mL of N,N'-dimethylformamide was added thereto and the mixture was cooled to 0° C. 20 mL of N,N'-dimethylformamide was mixed with Compound 1 (5.31 g, 40.2 mmol) and the mixture was charged in a dropping funnel and added dropwise over 30 minutes. After the completion of the dropwise addition, 20 mL of N,N'-dimethylformamide was mixed with Compound 13 (6.87 g, 28.7 mmol) and the mixture was charged in the same dropping funnel and added dropwise over 15 minutes. After the completion of the dropwise addition, the temperature of the reaction mixture was raised to 40° C., followed by stirring for 3 hours. After 3 hours, the disappearance of Compound 13 was confirmed by ESI-MS measurement, the reaction mixture was allowed to cool to room temperature. 150 mL of ethyl acetate was added to the reaction mixture and washed once with 100 mL of an aqueous saturated ammonium chloride solution and twice with 100 mL of an aqueous saturated sodium chloride solution. 15 g of sodium sulfate was added to the organic phase to dry, followed by filtration. The filtrate was concentrated under a reduced pressure to obtain Compound 14 as pale yellow colored transparent liquid.

Yield: 6.9 g

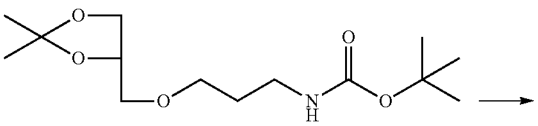

14

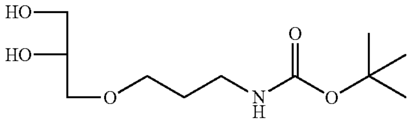

15

Compound 14 (6.90 g, 23.8 mmol), tetrahydrofuran (20 ml) and 1M hydrochloric acid (20 mL) were charged in an eggplant-shaped flask, and the mixture was stirred at room temperature for 2 hours. After 2 hours, the disappearance of Compound 14 was confirmed by ESI-MS measurement, and 50 mL of ethyl acetate was added to the reaction mixture. The mixed solution was washed twice with 50 mL of an aqueous saturated sodium chloride solution. 5 g of sodium sulfate was added to the organic phase to dry, followed by filtration. The filtrate was concentrated under a reduced pressure to obtain Compound 15 as pale yellow colored transparent liquid.

Yield: 1.7 g

MS ($ESI^+$): Compound 15 250.2 $[M+H]^+$ $^1$H-NMR ($CDCl_3$, 400 MHz): 4.83 (s, 1H), 3.85 (m, 1H), 3.70 (dd, 1H), 3.64 (dd, 1H), 3.51 (m, 4H), 3.25 (m, 2H), 1.74 (m, 2H), 1.44 (s, 9H)

Example 2-2

Synthesis of Compound 23 Represented by Formula (3) Wherein $Y^1$ is —O—$(CH_2)_3$—$NH_2$ and n is 24

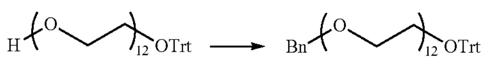

5 16

(in the formula, Bn represents a benzyl group and Trt represents a triphenylmethyl group.)

Sodium hydride (1.83 g) was charged in a 1-liter four-necked eggplant-shaped flask, followed by nitrogen purge. Washing with dehydrated hexane (20 mL) was performed twice, 80 mL of acetonitrile was added thereto and the mixture was cooled to 0° C. 40 mL of acetonitrile was mixed with Compound 5 (30.0 g, 38.0 mmol) which had been subjected to azeotropic dehydration three times with 20 mL of toluene and the mixture was charged in a dropping funnel and added dropwise over 30 minutes. After the completion of the dropwise addition, the temperature of the reaction mixture was raised to 40° C., followed by stirring for 30 minutes. Benzyl chloride (4.15 mL, 36.1 mmol) was charged in the same dropping funnel and added dropwise over 15 minutes. After the completion of the dropwise addition, the temperature of the reaction mixture was raised to 40° C., followed by stirring for 2 hours. After 2 hours, the disappearance of benzyl chloride was confirmed by using thin layer chromatography (hexane:ethyl acetate=4:1 by vol.) and the reaction mixture was allowed to cool to room temperature. After adding 20 mL of an aqueous saturated ammonium solution to the reaction mixture, the mixture was concentrated under a reduced pressure, and 100 ml of toluene was added the residue. The toluene solution was washed twice with 100 mL of an aqueous saturated ammonium chloride solution and once with 100 mL of an aqueous saturated sodium chloride solution. 10 g of sodium sulfate was added to the organic phase to dry, followed by filtration. The filtrate was concentrated under a reduced pressure to obtain Compound 16 as pale yellow colored transparent liquid.

Yield: 30.9 g

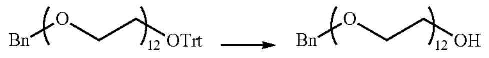

16 17

(in the formula, Bn represents a benzyl group and Trt represents a triphenylmethyl group.)

Compound 16 (30.9 g, 35.1 mmol) and methanol (240 mL) were charged in a 1-liter eggplant-shaped flask, then p-toluenesulfonic acid monohydrate (3.3 g, 17.6 mmol) and hexane (90 mL) were added thereto and the mixture was stirred at room temperature for 30 minutes. After 30 minutes, the hexane layer as the upper layer was removed, and then hexane (90 mL) was added thereto, followed by stirring at room temperature for 30 minutes. After the same operation was performed six times, the disappearance of Compound 16 was confirmed by ESI-MS measurement, and 100 mL of an aqueous saturated sodium bicarbonate solution was added thereto at 0° C. The mixed solution was washed twice with 90 mL of hexane. The solution of the product was concentrated under a reduced pressure, and the residue was dissolved in 100 mL of ion-exchanged water and washed twice with 100 mL of toluene. After adding 30 g of sodium chloride to the aqueous solution as the lower layer to achieve saturated concentration, extraction was performed twice with 100 mL of dichloromethane. 20 g of sodium sulfate was added to the organic phase extracted to dry, followed by filtration. The filtrate was concentrated under a reduced pressure to obtain Compound 17 as pale yellow colored transparent liquid.

Yield: 15.6 g

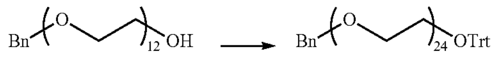

17 18

(in the formula, Trt represents a triphenylmethyl group and Bn represents a benzyl group.)

Sodium hydride (219 g, 50.2 mmol) was charged in a two-necked eggplant-shaped flask, followed by nitrogen purge. Washing with dehydrated hexane (25 mL×twice) was performed twice, 50 mL of acetonitrile was added thereto and the mixture was cooled to 0° C. Compound 17 (22.8 g, 35.8 mmol) was subjected to azeotropic dehydration three times with 15 mL of toluene, then mixed with 25 mL of acetonitrile and the mixture was charged in a dropping funnel and added dropwise over 30 minutes. 30 mL of acetonitrile was mixed with Compound 6 (52.8 g, 60.9 mmol) which had been subjected to azeotropic dehydration three times with 50 mL of toluene and the mixture was charged in the same dropping funnel and added dropwise over 15 minutes. After the completion of the dropwise addition, the temperature of the reaction mixture was raised to 80° C., followed by stirring for 2 hours. After 2 hours, the disappearance of Compound 16 was confirmed by ESI-MS measurement, and a methanol solution of sodium methoxide (3.5 mL) was added thereto, followed by stirring for 30 minutes. After 30 minutes, the disappearance of Compound 16 was confirmed by ESI-MS measurement and the reaction mixture was allowed to cool to room temperature. The reaction mixture was concentrated under a reduced pressure and 350 mL of toluene was added to the residue. The toluene solution was washed twice with 350 mL of an aqueous saturated ammonium chloride solution and once with 350 mL of an aqueous saturated sodium chloride solution. Sodium sulfate was added to the organic phase to dry, followed by filtration. The filtrate was concentrated under a reduced pressure to obtain Compound 18 as pale yellow colored transparent liquid.

Yield: 55.8 g

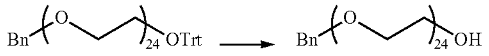

18 19

(in the formula, Trt represents a triphenylmethyl group and Bn represents a benzyl group.)

Compound 18 (55.8 g) and methanol (300 mL) were charged in an eggplant-shaped flask. p-Toluenesulfonic acid monohydrate (3.76 g, 19.8 mmol) and hexane (320 mL) were added thereto and the mixture was stirred at room temperature for 30 minutes. After 30 minutes, the hexane layer was removed, then hexane (200 mL) was added thereto, and the mixture was stirred at room temperature for 30 minutes. After the same operation was performed six times, the disappearance of Compound 18 was confirmed by ESI-MS measurement, and 300 mL of an aqueous saturated sodium bicarbonate solution was added thereto. The mixed solution was washed twice with 200 mL of hexane. The solution of the product was concentrated under a reduced pressure, 400 mL of dichloromethane was added to the residue and the mixture was washed three times with 400 mL of ion-exchanged water and once with 400 mL of an aqueous saturated sodium chloride solution. Sodium sulfate was added to the organic phase to dry, followed by filtration. The filtrate was concentrated under a reduced pressure to obtain Compound 19 as a white solid.

Yield: 39.3 g

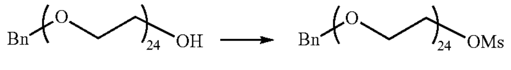

19 20

(in the formula, Bn represents a benzyl group and Ms represents a methanesulfonyl group.)

Compound 19 (14.7 g, 12.6 mmol) and toluene (70 ml) were charged in an eggplant-shaped flask. The inside of the eggplant-shaped flask was purged with nitrogen, and triethylamine (2.1 mL, 15.1 mmol) was added thereto. Methanesulfonyl chloride (1.1 mL, 13.9 mmol) was dropwise added at 0° C., and the mixture was stirred at room temperature for 2 hours. After 2 hours, the disappearance of Compound 19 was confirmed by ESI-MS measurement, and 70 mL of 1M hydrochloric acid was added thereto to cause liquid separation. The organic phase was washed once with 70 mL of 1M hydrochloric acid, twice with 70 mL of an aqueous saturated sodium bicarbonate solution and once with 70 mL of an aqueous saturated sodium chloride solution. Sodium sulfate was added to the organic phase to dry, followed by filtration. The filtrate was concentrated under a reduced pressure to obtain Compound 20 as a white solid.

Yield: 12.7 g

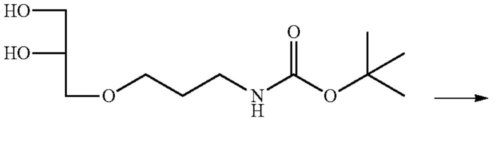

15

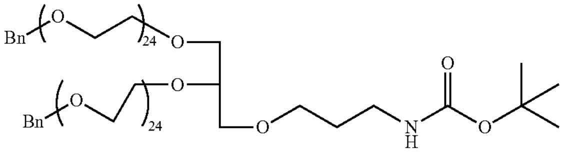

21

Compound 15 (0.82 g, 3.29 mmol) and Compound 20 (12.7 g, 10.2 mmol) were charged in an eggplant-shaped flask and subjected to toluene azeotrope (15 mL×2). Tetrahydrofuran (60 mL) was added thereto, and the inside of the eggplant-shaped flask was purged with nitrogen. Sodium hydroxide (408 mg, 10.2 mmol) was added thereto and the mixture was stirred under reflux with heating for 7 hours. After 7 hours, the disappearance of Compound 15 was confirmed by ESI-MS measurement, and 20 mL of an aqueous saturated ammonium chloride solution was added thereto to quench the reaction. The solution was concentrated under a reduced pressure (only tetrahydrofuran), and the residue was dissolved in 60 mL of toluene. The solution was washed once with 60 mL of an aqueous saturated ammonium chloride solution and once with 60 mL of an aqueous saturated sodium chloride solution. Sodium sulfate was added to the organic phase to dry, followed by filtration. The filtrate was concentrated under a reduced pressure to obtain Compound 21 as a white solid.

Yield: 8.5 g

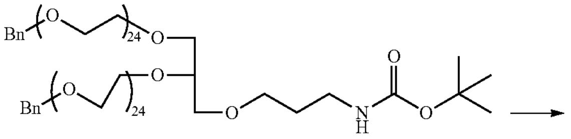

21

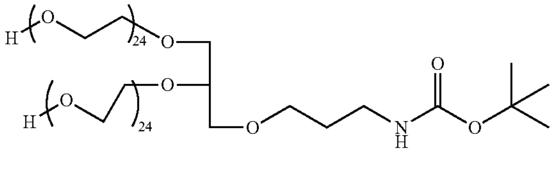

22

Compound 21 (8.5 g) and methanol (40 mL) were charged in an eggplant-shaped flask, and the inside of the eggplant-shaped flask was purged with nitrogen. Palladium carbon (900 mg) was added thereto, and the inside of the eggplant-shaped flask was purged with hydrogen, followed by stirring at room temperature for 5 hours. After 5 hours, the disappearance of Compound 21 was confirmed by ESI-MS measurement, and the reaction solution was filtered (glass fiber filter paper). The filtrate was concentrated under a reduce pressure, and the residue was dissolved in 40 mL of dichloromethane. The solution was washed three times with 40 mL of ion-exchanged water. Sodium sulfate was added to the organic phase to dry, followed by filtration. The filtrate was concentrated under a reduced pressure to obtain Compound 22 as a white solid.

Yield: 3.9 g

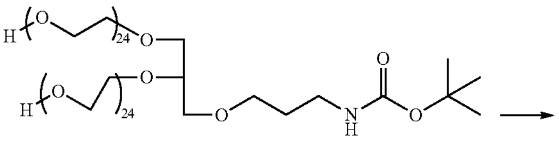

22

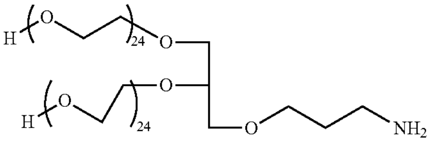

23

Compound 22 (3.9 g, 1.6 mmol) and dichloromethane (20 mL) were charged in an eggplant-shaped flask, and the inside of the eggplant-shaped flask was purged with nitrogen. Trifluoroacetic acid (0.15 mL, 1.9 mmol) was added thereto at 0° C., and the mixture was stirred at room temperature for 5 hours. After 5 hours, the disappearance of Compound 22 was confirmed by ESI-MS measurement, and triethylamine (0.31 mL, 2.2 mmol) was added thereto to quench the reaction. The solution was extracted three times with 20 mL of 1M hydrochloric acid. The aqueous phases were put together and extracted three times with 20 mL of dichloromethane. The organic phases were put together, and sodium sulfate was added thereto to dry, followed by filtration. The filtrate was concentrated under a reduced pressure to obtain Compound 23 as pale yellow colored transparent liquid.

Yield: 3.4 g

Example 2-3

Synthesis of Compound 25 Represented by Formula (1) Wherein $X^1$ is Azide Group, $Y^1$ is Bromoacetamide Group, $L^1$ is $-(CH_2)_2-$, $L^2$ is Ether Bond, $L^3$ is $-O-(CH_2)_3-$ and n is 23

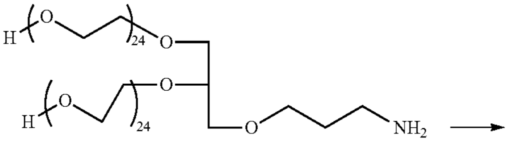

23

-continued

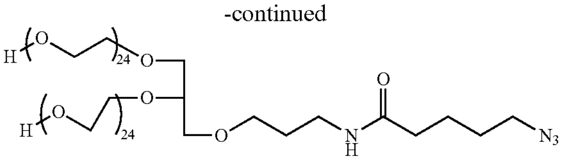

24

Compound 23 (1.0 g, 0.44 mmol), 5-azidopentanoic acid (68.7 mg, 0.48 mmol) and chloroform (5 mL) were charged in an eggplant-shaped flask. 1-(3-dimethylaminopropyl)-3-ethylcarbodiimide hydrochloride (104 mg, 0.53 mmol) was added thereto and the mixture was stirred at room temperature for 4 hours. After 4 hours, the disappearance of Compound 23 was confirmed by ESI-MS measurement, and the reaction solution was filtered. The filtrate was washed three times with 5 mL of an aqueous saturated sodium bicarbonate solution and once with 5 mL of an aqueous saturated sodium chloride solution. Magnesium sulfate was added thereto to dry, followed by filtration. The filtrate was concentrated under a reduced pressure to obtain Compound 24 as a white solid.

Yield 1.0 g

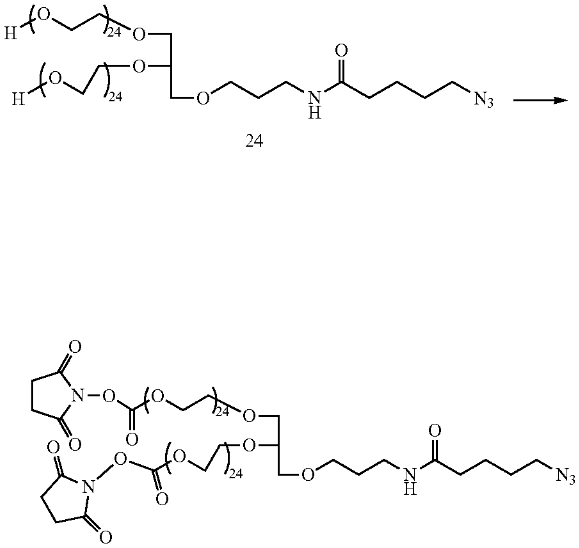

24

25

Compound 24 (1.0 g 0.42 mmol), triethylamine (0.32 mL, 1.0 mmol), dibutylhydroxytoluene (3 mg, 0.014 mmol) and dichloromethane (50 mL) were charged in an eggplant-shaped flask. Disuccinimidyl carbonate (237 mg, 0.92 mmol) was added thereto and the mixture was stirred at room temperature for 5 hours. After 5 hours, the disappearance of Compound 24 was confirmed by ESI-MS measurement, and 50 mL of an aqueous sodium chloride solution (pH=2.0) was added thereto to cause liquid separation. The organic phase was washed with 50 mL of an aqueous sodium chloride solution (pH=2.0) and concentrated under a reduced pressure. 50 mL of 1M hydrochloric acid was added to the residue, the mixture was washed twice with 50 mL of ethyl acetate, and the aqueous phase was extracted twice with 50 mL of dichloromethane. The organic phases were put together, washed twice with 50 mL of an aqueous 20% sodium chloride solution, then the organic phases were put together, and magnesium sulfate was added thereto to dry, followed by filtration. The filtrate was concentrated under a reduced pressure to obtain Compound 25 as a white solid.

Yield: 1.0 g

MS (ESI$^+$): Compound 25 1352.6 $[M+2NH_4]^{2+}$ $^1$H-NMR ($CD_3OD$, 400 MHz): 4.43 (m, 4H), 3.64 (m, 195H), 3.41 (m, 2H), 3.22 (m, 2H), 2.80 (s, 8H), 2.71 (t, 2H), 1.74 (m, 2H), 1.46 (m, 4H)

Example 3-1

Synthesis of Compound 27 Represented by Formula (1) Wherein $X^1$ is Active Carbonate Group, $Y^1$ is Bromoacetamide Group, $L^2$ is Ether Bond and n is 12

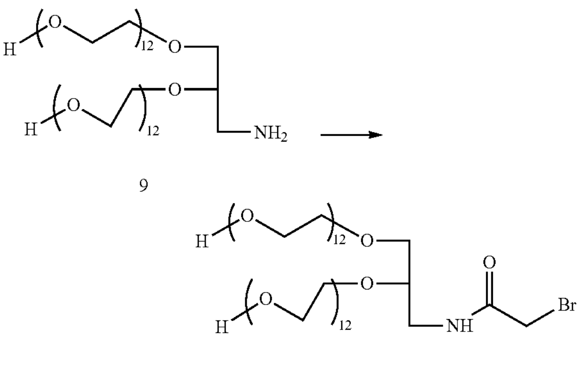

9

26

Compound 9 (1.0 g, 0.87 mmol) obtained in Example 1-2 and toluene (5 mL) were charged in an eggplant-shaped flask. The inside of the eggplant-shaped flask was purged with nitrogen and triethylamine (0.145 mL, 1.04 mmol) was added thereto. Bromoacetylbromide (0.083 mL, 0.95 mmol) was dropwise added thereto at 0° C. and the mixture was stirred at room temperature for 2 hours. After 2 hours, the disappearance of Compound 9 was confirmed by ESI-MS measurement, and 5 mL of 1M hydrochloric acid was added thereto to cause liquid separation. The organic phase was washed once with 5 mL of 1M hydrochloric acid, twice with 5 mL of an aqueous saturated sodium bicarbonate solution and once with 5 mL of an aqueous saturated sodium chloride solution. Sodium sulfate was added to the organic phase to dry, followed by filtration. The filtrate was concentrated under a reduced pressure to obtain Compound 26 as pale yellow colored transparent liquid.

Yield: 1.03 g

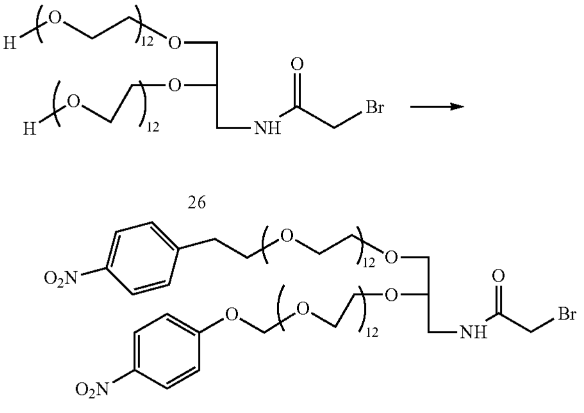

26

27

Compound 26 (1.03 g, 0.81 mmol) and toluene (5 mL) were charged in an eggplant-shaped flask. The inside of the eggplant-shaped flask was purged with nitrogen and triethylamine (0.27 mL, 1.94 mmol) was added thereto. 4-Nitrophenyl chloroformate (359 mg, 1.78 mmol) was added thereto at 0° C. and the mixture was stirred at room temperature for 2 hours. After 2 hours, the disappearance of Compound 26 was confirmed by ESI-MS measurement, and 5 mL of 1M hydrochloric acid was added thereto to cause liquid separation. The organic phase was washed once with 5 mL of 1M hydrochloric acid and once with 5 mL of an aqueous saturated sodium chloride solution. Sodium sulfate was added to the organic phase to dry, followed by filtration. The filtrate was concentrated under a reduced pressure to obtain Compound 27 as a white solid.

Yield: 1.20 g

MS ($ESI^+$): Compound 27 816.8 $[M+2NH_4]^{2+}$ $^1$H-NMR ($CD_3OD$, 400 MHz): 8.37 (d, 2H), 7.44 (d, 2H), 4.31 (m, 4H), 4.10 (s, 2H), 3.64 (m, 95H), 3.41 (m, 2H)

Example 4-1

Synthesis of Compound 31 Represented by Formula (1) Wherein $X^1$ is Active Ester Group, $Y^1$ is Alkynyl Group, $L^1$ is —$(CH_2)_2$—, $L^2$ is Ether Bond, $L^3$ is —NHC(O)—$(CH_2)_2$— and n is 12

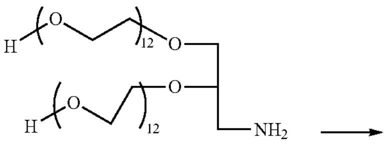

9

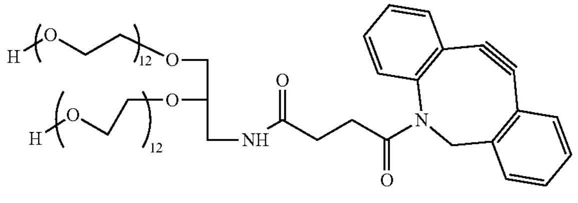

28

Dibenzocyclooctyne-N-hydroxysuccinimidyl ester (198 mg, 0.48 mmol) and chloroform (2 mL) were charged in an eggplant-shaped flask. Compound 9 (500 mg, 0.44 mmol) obtained in Example 1-2 and triethylamine (0.072 mL, 0.52 mmol) were dissolved in chloroform (1 mL) and the solution was dropwise added to the flask at room temperature. After stirring at room temperature for 4 hours, the disappearance of dibenzocyclooctyne-N-hydroxysuccinimidyl ester was confirmed by ESI-MS measurement, 5 mL of 1M hydrochloric acid was added thereto to cause liquid separation. The organic phase was washed with 5 mL of 1M hydrochloric acid and 5 mL of an aqueous saturated sodium chloride solution, and concentrated under a reduced pressure. Magnesium sulfate was added to the organic phase to dry, followed by filtration. The filtrate was concentrated under a reduced pressure to obtain Compound 28 as a white solid.

Yield: 613 mg

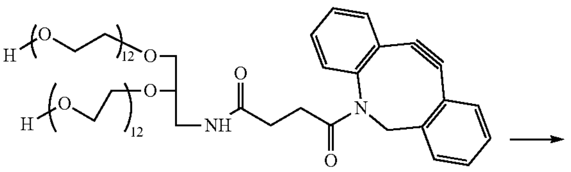

28

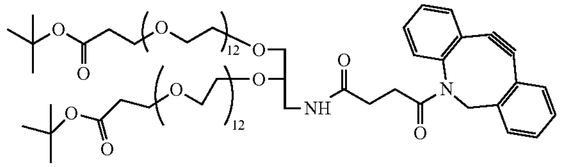

29

Compound 28 (613 mg, 0.43 mmol) and methylene chloride (12 mL) were charged in an eggplant-shaped flask. Potassium hydroxide (powder, 24 mg, 0.43 mmol) was added thereto at 0° C., tert-butyl acrylate (0.38 mL, 2.58 mmol) was dropwise added thereto, and the mixture was stirred at 0° C. for 1.5 hours. After 1.5 hours, the progress of the reaction was confirmed by ESI-MS measurement, and after 2 hours, 5 mL of an aqueous saturated ammonium chloride solution was added. The mixed solution was subjected to liquid separation and the organic phase was washed once with 5 mL of an aqueous saturated sodium chloride solution. Magnesium sulfate was added to the organic phase to dry, followed by filtration. The filtrate was concentrated under a reduced pressure to obtain Compound 29 as pale yellow colored transparent liquid.

Yield: 715 mg

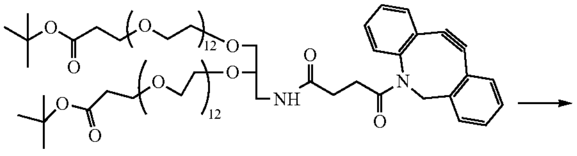

29

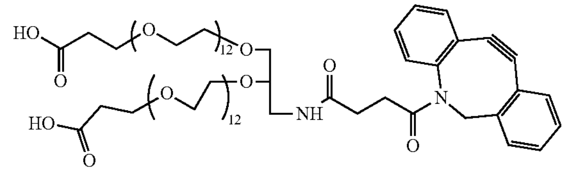

30

Compound 29 (715 mg, 0.42 mmol) and 1M hydrochloric acid (3 mL) were charged in an eggplant-shaped flask, and the mixture was stirred at 60° C. for 2 hours. After 2 hours, the disappearance of Compound 29 was confirmed by ESI-MS measurement, and the mixture was cooled to room temperature. 5 mL of dichloromethane was added to the reaction solution to cause liquid separation. The organic phase was washed once with 5 mL of an aqueous saturated sodium bicarbonate solution and once with an aqueous saturated sodium chloride solution. Magnesium sulfate was added to the organic phase to dry, followed by filtration. The filtrate was concentrated under a reduced pressure to obtain Compound 30 as a white solid.

Yield: 641 mg

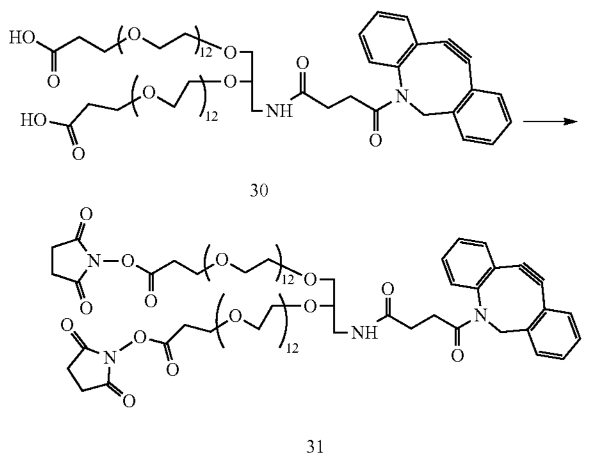

Compound 30 (641 mg, 0.41 mmol), N-hydroxysuccinimide (112 mg, 0.97 mmol) and chloroform (5 mL) were charged in an eggplant-shaped flask. 1-(3-dimethylaminopropyl)-3-ethylcarbodiimide hydrochloride (202 mg, 1.05 mmol) was added thereto and the mixture was stirred at room temperature for 4 hours. After 4 hours, the disappearance of Compound 30 was confirmed by ESI-MS measurement, and the reaction solution was filtered. The filtrate was washed three times with 5 mL of citric acid buffer (pH=3.0) and once with 5 mL of an aqueous saturated sodium chloride solution. Magnesium sulfate was added thereto to dry, followed by filtration. The filtrate was concentrated under a reduced pressure to obtain Compound 31 as a white solid.

Yield: 633 mg

MS ($ESI^+$): Compound 31 904.3 $[M+2NH_4]^{2+}$ $^1$H-NMR ($CD_3OD$, 400 MHz): 7.48 (m, 8H), 5.13 (d, 1H), 3.64 (m, 104H), 3.40 (m, 2H), 2.98 (m, 4H), 2.83 (s, 8H), 2.66 (t, 4H)

<Chain Length Purity and Functional Group Purity of Branched Type Hetero Monodispersed Polyethylene Glycol Represented by Formula (1)>

Example 5-1

[Measurement of Chain Length Purity]

As the chain length purity of Compound 11 synthesized in Example 1-3, the chain length purity of Compound 9 synthesized in Example 1-2 was used.

As a result of reverse phase chromatography measurement of Compound 9, it was found that 93.4% of a branched type monodispersed polyethylene glycol having n representing a number of repeating units of a monodispersed polyethylene glycol of 12 and 6.6% in total of compounds having n other than 12 were contained so that the chain length purity was 93.4%. The results were summarized in Table 1.

Additionally, in the reverse phase chromatography measurement, identification of the respective peaks is performed by using a mass spectrometer as a detector, and then the purity is determined from the area values of the respective peaks calculated by using a differential refractometer as a detector. In the case of using a mass spectrometer as a detector, the measurement was carried out by using Alliance 2695 manufactured by Waters Corp. as an equipment, Quattro micro tandem mass spectrometer manufactured by Waters Corp. as an detector (mass spectrometer), TSKgel ODS-80Ts (particle diameter: 5 μm, column size: 4.6 mm×25 cm) manufactured by Tosoh Corp. as a column, and 5 mM ammonium acetate in methanol/distilled water=45/55 as a developing solvent, respectively, under conditions of flow rate of 0.6 mL/min, column temperature of 45° C., sample concentration of 0.01 mg/g, and injection volume of 5 μL. In the case of using a differential refractometer as a detector, the measurement was carried out by using build GPC system HLC-8220 manufactured by Tosoh Corp. as an equipment, RI-8020 manufactured by Tosoh Corp. as a detector (differential refractometer), TSKgel ODS-80 Ts (particle diameter: 5 μm, column size: 4.6 mm×25 cm) manufactured by Tosoh Corp. as a column, and 5 mM ammonium acetate in methanol/distilled water=45/55 as a developing solvent, respectively, under conditions of flow rate of 0.6 mL/min, column temperature of 45° C., sample concentration of 0.2 mg/mL and injection volume of 40 μL.

[Measurement of Functional Group Purity]

The functional group purity of Compound 11 synthesized in Example 1-3 was determined by $^1$H-NMR measurement based on the functional group purity of Compound 9.

Specifically, as a result of reverse phase chromatography measurement of Compound 9, it was found that 99.9% of the compound having two hydroxyl groups and one amino group at the terminals and 0.1% of the compounds having other combinations of the terminal functional groups were contained so that the functional group purity was 99.9%. Further, in the reaction for obtaining Compound 10 from Compound 9, the peaks (3.16, 3.04 ppm, 2H) based on the methylene group at α-position of the amino group of Compound 9 were disappeared and new peaks were observed at 3.38 and 3.18 ppm. When the peak (3.62 ppm, 97H) whose integral value did not change in the reaction was taken as the standard, the integral value of the new peaks was 1.997 in total so that the introduction rate of maleimide group was 99.9% (=1.997÷2×100).

Subsequently, when the integral value of the peak (6.83 ppm, 2H) based on the maleimide group in the $^1$H-NMR spectrum of Compound 11 was taken as the standard (2.0), the integral value of the peak (4.47 ppm, 4H) based on the active carbonate group was 3.840, thus the introduction rate of active carbonate group was 96.0% (=3.840÷4). Therefore, the functional group purity of Compound 11 was 95.8% (=99.9×0.999×0.96). The results were summarized in Table 1.

Example 5-2

[Measurement of Chain Length Purity]

As the chain length purity of Compound 25 synthesized in Example 2-3, the chain length purity of Compound 23 synthesized in Example 2-2 was used.

As a result of reverse phase chromatography measurement of Compound 23, it was found that 91.6% of a branched type monodispersed polyethylene glycol having n representing a number of repeating units of a monodispersed polyethylene glycol of 24 and 8.4% in total of compounds having n other than 24 were contained so that the chain length purity was 91.6%. The results were summarized in Table 1. The reverse phase chromatography measurement was carried out by the same method as in Example 5-1 except for using 5 mM ammonium acetate in methanol/distilled water=55/45 as the developing solvent.

[Measurement of Functional Group Purity]

The functional group purity of Compound 25 synthesized in Example 2-3 was determined by $^1$H-NMR measurement in the same manner as in Example 7-1.

As a result of reverse phase chromatography measurement of Compound 23, the functional group purity was 99.9%. Further, in the reaction for obtaining Compound 24 from Compound 23, the peak (3.10 ppm, 2H) based on the methylene group at α-position of the amino group of Compound 23 was disappeared and a new peak was observed at 3.41 ppm. When the peak (3.64 ppm, 195H) whose integral value did not change in the reaction was taken as the standard, the integral value of the new peak was 1.990 in total so that the introduction rate of azide group was 99.5% (=1.990÷2×100). Subsequently, when the integral value of the peak (3.22 ppm, 2H) based on the azide group in the $^1$H-NMR spectrum of Compound 25 was taken as the standard (2.0), the integral value of the peak (4.43 ppm, 4H) based on the active carbonate group was 3.905, thus the introduction rate of active carbonate group was 97.6% (=3.905÷4). Therefore, the functional group purity of Compound 25 was 97.0% (=99.9×0.995×0.976). The results were summarized in Table 1.

Example 5-3

[Measurement of Chain Length Purity]

The chain length purity of Compound 27 synthesized in Example 3-1 was determined by the same method as in Example 5-1. The chain length purity was 93.4%. The results were summarized in Table 1.

[Measurement of Functional Group Purity]

The functional group purity of Compound 27 synthesized in Example 3-1 was determined by $^1$H-NMR measurement in the same manner as in Example 5-1.

As a result of reverse phase chromatography measurement of Compound 9, the functional group purity was 99.9%. Further, in the reaction for obtaining Compound 26 from Compound 9, the peaks (3.16, 3.04 ppm, 2H) based on the methylene group at α-position of the amino group of Compound 9 were disappeared and a new peak was observed at 3.41 ppm. When the peak (3.62 ppm, 97H) whose integral value did not change in the reaction was taken as the standard, the integral value of the new peak was 1.992 so that the introduction rate of bromoacetamide group was 99.6% (=1.992÷2×100). Subsequently, when the integral value of the peak (4.13 ppm, 2H) based on the bromoacetamide group in the $^1$H-NMR spectrum of Compound 27 was taken as the standard (2.0), the integral value of the peak (4.31 ppm, 4H) based on the active carbonate group was 3.896. Thus, the introduction rate of active carbonate group was 97.4% (=3.896÷4). Therefore, the functional group purity of Compound 27 was 96.9% (=99.9×0.996×0.974). The results were summarized in Table 1.

Example 5-4

[Measurement of Chain Length Purity]

The chain length purity of Compound 31 synthesized in Example 4-1 was determined by the same method as in Example 5-1. The chain length purity was 93.4%.

[Measurement of Functional Group Purity]

The functional group purity of Compound 31 synthesized in Example 4-1 was determined by $^1$H-NMR measurement.

As a result of reverse phase chromatography measurement of Compound 30, the functional group purity was 99.9%. Further, in the reaction for obtaining Compound 28 from Compound 9, the peaks (3.16, 3.04 ppm, 2H) based on the methylene group at α-position of the amino group of Compound 9 were disappeared and a new peak was observed at 3.40 ppm. When the peak (3.62 ppm, 97H) whose integral value did not change in the reaction was taken as the standard, the integral value of the new peak was 1.998 so that the introduction rate of alkynyl group was 99.9% (=1.998÷2×100). Subsequently, when the integral value of the peak (2.98 ppm, 4H) based on the alkynyl group in the $^1$H-NMR spectrum of Compound 31 was taken as the standard (4.0), the integral value of the peak (2.83 ppm, 8H) based on the active ester group was 7.624. Thus, the introduction rate of active ester group was 95.3% (=7.624÷8). Therefore, the functional group purity of Compound 31 was 95.1% (=99.9×0.999×0.953). The results were summarized in Table 1.

TABLE 1

| Sample | | Chain Length Purity (%) | Functional Group Purity (%) |
|---|---|---|---|
| Example 5-1 | Compound 11 Obtained in Example 1-3 | 93.4 | 95.8 |
| Example 5-2 | Compound 25 Obtained in Example 2-3 | 91.6 | 97.5 |
| Example 5-3 | Compound 27 Obtained in Example 3-1 | 93.4 | 96.9 |
| Example 5-4 | Compound 31 Obtained in Example 4-1 | 93.4 | 95.2 |

Chain Length Purity and Functional Group Purity of Intermediate for Production of Branched Type Hetero Monodispersed Polyethylene Glycol Represented by Formula (3)

Example 6-1

Compound 9 was obtained in the same manner as in Example 1-2 except for using sodium hydroxide in place of potassium hydroxide as the base catalyst in the reaction between Compound 4 and Compound 6. The molar yield of three steps based on Compound 4 was 48.3%. The results were summarized in Table 2.

Example 6-2

Compound 9 was obtained in the same manner as in Example 1-2 except for using potassium tert-butoxide in place of potassium hydroxide as the base catalyst in the reaction between Compound 4 and Compound 6. The molar yield of three steps based on Compound 4 was 50.1%. The results were summarized in Table 2.

Example 7-1

The purity of Compound 9 synthesized in Example 1-2 was determined by reverse phase chromatography measurement.

The measurement conditions were same as those in Example 5-1. As a result, 93.4% of a branched type monodispersed polyethylene glycol having n representing a number of repeating units of a monodispersed polyethylene glycol of 12 and 6.6% in total of compounds having n other than 12 were contained so that the chain length purity was 93.4%. Further, 99.9% of the compound having two hydroxyl groups and one amino group at the terminals and 0.1% of the compounds having other combinations of the terminal functional groups were contained so that the functional group purity was 99.9%. The results were summarized in Table 2.

Example 7-2

The purity of Compound 9 synthesized in Example 6-1 was determined by the same method as in Example 5-1. The chain length purity was 91.8% and the functional group purity was 99.9%. The results were summarized in Table 2.

Example 7-3

The chain length purity of Compound 9 synthesized in Example 6-2 was determined by the same method as in Example 5-1. The chain length purity was 92.6% and the functional group purity was 99.7%. The results were summarized in Table 2.

Reference Example 1-1: Case where Base Catalyst in Step (1) was Changed

Compound 9 was obtained in the same manner as in Example 1-2 except for using sodium hydride in place of potassium hydroxide as the base catalyst in the reaction between Compound 4 and Compound 6. The molar yield of three steps based on Compound 4 was 23.2%. The results were summarized in Table 2.

Reference Example 1-2: Case where Liquid Separation Temperature in Step (3) was Changed Compound 9 was obtained in the same manner as in Example 1-2 except for changing the temperature at the separatory washing to 25° C. The molar yield of three steps based on Compound 4 was 52.8%. The results were summarized in Table 2.

Reference Example 1-3: Case where Combination of Protective Group a and Functional Group Z is not Preferred Compound 9 was obtained in the same manner as in Example 1-2 except for using Compound 32 in place of Compound 6. The molar yield of three steps based on Compound 4 was 36.2%. The results were summarized in Table 2.

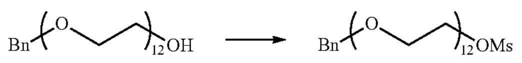

17 32

(in the formula, Bn represents a benzyl group and Ms represents a methanesulfonyl group.)

Compound 17 (15.6 g, 24.5 mmol) and toluene (80 ml) were charged in an eggplant-shaped flask. The inside of the eggplant-shaped flask was purged with nitrogen, and triethylamine (4.1 mL, 29.4 mmol) was added thereto. Methanesulfonyl chloride (2.1 mL, 27.0 mol) was dropwise added thereto at 0° C., and the mixture was stirred at room temperature for 2 hours. After 2 hours, the disappearance of Compound 17 was confirmed by ESI-MS measurement, and 80 mL of 1M hydrochloric acid was added thereto to cause liquid separation. The organic phase was washed once with 80 mL of 1M hydrochloric acid, twice with 80 mL of an aqueous saturated sodium bicarbonate solution and once with 80 mL of an aqueous saturated sodium chloride solution. Sodium sulfate was added to the organic phase to dry, followed by filtration. The filtrate was concentrated under a reduced pressure to obtain Compound 32 as pale yellow colored transparent liquid.

Yield: 16.7 g

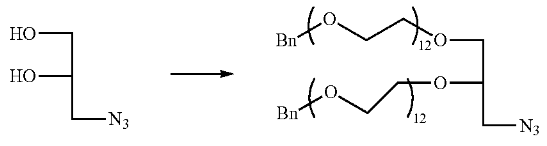

4 33

(in the formula, Bn represents a benzyl group.)

Compound 4 (1.64 g, 14.0 mmol) and Compound 32 (30.0 g, 42.0 mmol) were charged in an eggplant-shaped flask and subjected to toluene azeotrope (30 mL×2). Tetrahydrofuran (270 mL) was added thereto, and the inside of the eggplant-shaped flask was purged with nitrogen. Potassium hydroxide (powder, 2.36 g, 42 mmol) was added thereto and the mixture was stirred under reflux with heating for 7 hours. After 7 hours, the disappearance of Compound 4 was confirmed by ESI-MS measurement, and 10 mL of an aqueous saturated ammonium chloride solution was added thereto to quench the reaction. The solution was concentrated under a reduced pressure (only tetrahydrofuran), and the residue was dissolved in 150 mL of toluene. The solution was washed twice with 100 mL of ion-exchanged water, once with 100 mL of an aqueous saturated sodium bicarbonate solution and once with 100 mL of an aqueous saturated sodium chloride solution. Sodium sulfate was added to the organic phase to dry, followed by filtration. The filtrate was concentrated under a reduced pressure to obtain Compound 33 as pale yellow colored transparent liquid.

Yield: 30.2 g

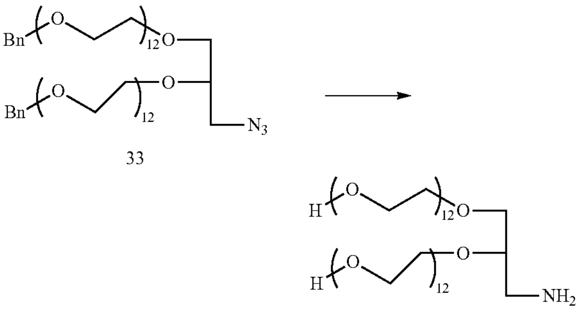

33 9

(in the formula, Bn represents a benzyl group.)

Compound 33 (30.2 g) and methanol (150 mL) were charged in an eggplant-shaped flask, and the inside of the eggplant-shaped flask was purged with nitrogen. Palladium carbon (3.0 g) was added thereto, and the inside of the eggplant-shaped flask was purged with hydrogen, followed by stirring at room temperature for 5 hours. After 5 hours, the disappearance of Compound 33 was confirmed by ESI-MS measurement, and the reaction solution was filtered (glass fiber filter paper). The filtrate was concentrated under a reduce pressure, and the residue was dissolved in 150 mL of dichloromethane. The solution was washed five times with 150 mL of ion-exchanged water. Sodium sulfate was added to the organic phase to dry, followed by filtration. The filtrate was concentrated under a reduced pressure to obtain Compound 9 as pale yellow colored transparent liquid. The molar yield of two steps based on Compound 4 was 36.2%. The results were summarized in Table 2.

Yield: 5.8 g

Reference Example 2-1

The purity of Compound 9 synthesized in Reference Example 1-1 was determined by the same method as in Example 9-1. The chain length purity was 64.9% and the functional group purity was 70.4%. The results were summarized in Table 2.

Reference Example 2-2

The purity of Compound 9 synthesized in Reference Example 1-2 was determined by the same method as in Example 9-1. The chain length purity was 86.1% and the functional group purity was 92.2%. The results were summarized in Table 2.

Reference Example 2-3

The purity of Compound 9 synthesized in Reference Example 1-3 was determined by the same method as in Example 9-1. The chain length purity was 92.7% and the functional group purity was 99.30. The results were summarized in Table 2.

TABLE 2

| Sample | | Molar Yield (%) | Chain Length Purity (%) | Functional Group Purity (%) |
|---|---|---|---|---|
| Example 7-1 | Compound 9 Obtained in Example 1-2 | 51.0 | 93.4 | 99.9 |
| Example 7-2 | Compound 9 Obtained in Example 6-1 | 48.3 | 91.8 | 99.9 |
| Example 7-3 | Compound 9 Obtained in Example 8-2 | 50.1 | 92.6 | 99.7 |
| Reference Example 2-1 | Compound 9 Obtained in Reference Example 1-1 | 23.2 | 84.9 | 70.4 |
| Reference Example 2-2 | Compound 9 Obtained in Reference Example 1-2 | 52.8 | 86.1 | 92.2 |
| Reference Example 2-3 | Compound 9 Obtained in Reference Example 1-3 | 36.2 | 92.7 | 99.3 |

From the results described above, it was confirmed that in Compound 9 obtained in Example 1-2, Example 6-1 or Example 6-2, the purity (chain length purity) of the compound in which n which represents a number of repeating units of a monodispersed polyethylene glycol was 12 was 90% or more and the purity (functional group purity) of the compound having two hydroxyl groups and one amino group at the terminals was 9500 or more.

Further, as to Compound 9 obtained in Reference Example 1-1, because of using sodium hydride as the base catalyst in the coupling of step (1), due to decomposition of the branch site or side reaction a plurality of impurities having unknown structures were generated so that the molar yield, chain length purity and functional group purity were decreased. In the case of synthesizing the compound represented by formula (1) described above using Compound 9 obtained in Reference Example 1-1, the compound having low chain length purity and low functional group purity is obtained and when purification by column chromatography is carried out for increase in the purity, the molar yield is further decreases.

Moreover, as to Compound 9 obtained in Reference Example 1-2, because of high temperature in the separatory purification in Step (3), the monodispersed polyethylene glycol represented by formula (39) described above was not separated. Since the impurity was a straight-chain type and the terminal functional groups were a combination of a hydroxyl group and a mesylate group, the chain length purity and functional group purity of Compound 9 were decreased.

In the case of obtaining Compound 11, for example, in the same manner as in Example 1-3 using Compound 9 obtained in Reference Example 1-2, since the impurity described above forms a compound which is a straight-chain type and has an active carbonate group and a mesylate group at the terminals, the chain length purity and functional group purity of Compound 11 are decreased. When purification by column chromatography is carried out for increase in the purity, the molar yield is decreases.

Furthermore, as to Compound 9 obtained in Reference Example 1-3, because the deprotection of the protective group A (benzyl group) and the reduction treatment of the functional group $Z^1$ (azide group) of the compound represented by formula (6) described above were carried out at the same time in step (2), the compound represented by formula (3) described above was dissolved in the aqueous phase together with the monodispersed polyethylene glycol represented by formula (39) described above in the separatory purification of step (3) so that the molar yield was decreased. In the case of synthesizing the compound represented by formula (1) described above using Compound 9 obtained in Reference Example 1-3, the chain length purity is 90% or more and the functional group purity is 95% or more, but the molar yield is low.

Example 8-1

Synthesis of Compound 45 Represented by Formula (40) Wherein $Y^2$ is —$NH_2$ and n is 12

(46)

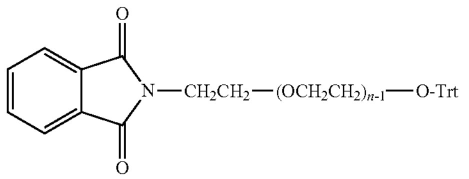

(in the formula, Trt represents a triphenylmethyl group.)

Compound 15 (15 g, 19.0 mmol) and dichloromethane (71 mL) were charged in an eggplant-shaped flask to be dissolved. The inside of the eggplant-shaped flask was purged with nitrogen, and phthalimide (3.92 g, 26.6 mmol) and triphenyl phosphine (6.98 g, 26.6 mmol) were added thereto. Diisopropyl azodicarboxylate (4.61 g, 22.8 mmol) dissolved in dichloromethane (15 mL) was dropwise added thereto from 20 to 30° C. and the mixture was stirred at 25° C. for one hour. After one hour, the disappearance of Compound 5 was confirmed by thin layer chromatography (TLC) measurement, and methanol (0.73 mL, 22.8 mmol) was added thereto to terminate the reaction. The reaction solution was concentrated under a reduced pressure to obtain Compound 46 as transparent liquid.

$$NH_2—CH_2CH_2—(OCH_2CH_2)_{n-1}—O\text{-}Trt \quad (47)$$

(in the formula, Trt represents a triphenylmethyl group.)

The total amount of Compound 46 described above, methanol (59.4 mL) and ethylenediamine monohydrate (22.28 g, 285 mmol) were charged in an eggplant-shaped flask, followed by nitrogen purge to be dissolved. The mixture was stirred from 35 to 45° C. for one hour. After one hour, the disappearance of Compound 46 was confirmed by NMR measurement. Toluene (75 mL) and an aqueous 20% sodium chloride solution (75 mL) were added to wash three times, and the organic phase was concentrated under a reduced pressure. Then, the residue was dissolved in ion-exchanged water (45 mL) and an aqueous 5% dihydrogen sodium phosphate solution (120 mL) was added thereto to adjust pH to 6. The solution was washed three times with ethyl acetate (190 mL) to obtain an aqueous solution of Compound 47.

$$NH_2—CH_2CH_2—(OCH_2CH_2)_{n\text{-}1}—OH \quad (48)$$

A small amount of 6N hydrochloric acid was added to the total volume of the aqueous solution of Compound 47 described above in an eggplant-shaped flask to adjust pH to 1 and the mixture was stirred for 5 hours. After 5 hours, the disappearance of Compound 47 was confirmed by thin layer chromatography (TLC) measurement, and the solid deposited was filtered off. pH was adjusted to 7.5 with a small amount of an aqueous 400 g/L sodium hydroxide solution and chloroform (200 mL) was added thereto to wash once. Sodium chloride was added to the resulting aqueous solution to form an aqueous saturated sodium chloride solution and chloroform (45 mL) and isopropanol (15 mL) were added thereto to extract the desired compound into the organic phase, and the organic phase was concentrated under a reduced pressure, dissolved again in chloroform (75 mL) and anhydrous sodium sulfate (10 g) was added thereto to dehydrate. The solution was filtered to remove the anhydrous sodium sulfate and concentrated under a reduced pressure while adding toluene (35 mL) to obtain Compound 48 as transparent liquid.

Yield: 6.51 g (49)

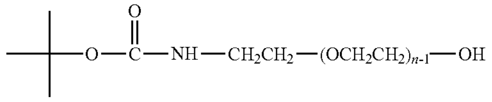

Compound 48 (5.93 g, 10.9 mmol), water (30 mL) and tetrahydrofuran (33 mL) were charged in an eggplant-shaped flask to be dissolved. The inside of the eggplant-shaped flask was purged with nitrogen, sodium hydrogen carbonate (2.66 g, 31.6 mmol) and di-tert-butyl dicarboxylate (3.46 g, 15.8 mmol) were added thereto, and the mixture was stirred from 20 to 30° C. for 6 hours. After 6 hours, the disappearance of Compound 48 was confirmed by thin layer chromatography (TLC) measurement. Hexane (45 mL) was added to wash the aqueous phase four times, and then dichloromethane (22.4 mL) was added thereto to extract the desired compound into the organic phase. Anhydrous sodium sulfate (6 g) was added to the organic phase to dehydrate and the solution was filtered to remove the anhydrous sodium sulfate. Then, the solution was concentrated under a reduced pressure to obtain Compound 49 as transparent liquid.

Yield: 6.31 g (50)

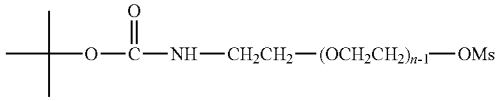

(in the formula, Ms represents a methanesulfonyl group.)

Compound 49 (6.2 g, 9.6 mmol) and toluene (36 mL) were charged in an eggplant-shaped flask to be dissolved. The inside of the eggplant-shaped flask was purged with nitrogen, triethylamine (1.33 g, 13.1 mmol) and methane sulfonyl chloride (1.29 g, 11.3 mmol) were added thereto, and the mixture was stirred from 20 to 30° C. for 4 hours. After 4 hours, the disappearance of Compound 49 was confirmed by thin layer chromatography (TLC) measurement. A 25% aqueous ammonia solution (30 mL) was added thereto to wash the organic phase three times and then an aqueous saturated sodium chloride solution (30 mL) was added thereto to wash the organic phase once. Anhydrous sodium sulfate (6 g) was added to the organic phase to dehydrate and the solution was filtered to remove the anhydrous sodium sulfate. Then, the solution was concentrated under a reduced pressure to obtain Compound 50 as transparent liquid.

Yield: 5.87 g

[Step (1')]

(51)

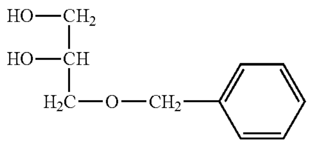

(52)

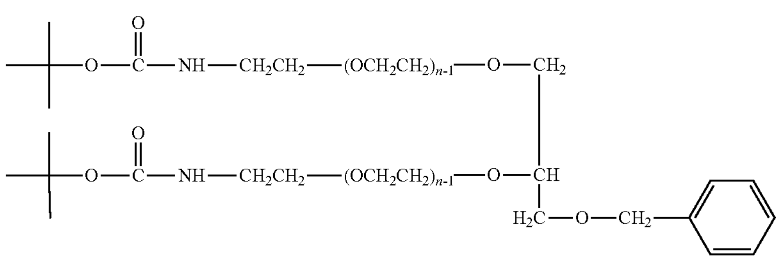

Compound 50 (4.0 g, 5.5 mmol), Compound 51 (0.47 g, 2.6 mmol) and dehydrated tetrahydrofuran (6.0 mL) were charged in an eggplant-shaped flask, and the inside of the eggplant-shaped flask was purged with nitrogen to be dissolved. Potassium hydroxide (powder, 0.15 g) was added thereto and the mixture was stirred from 20 to 30° C. for 2 hours. After 2 hours, the remaining of Compound 50 was confirmed by NMR measurement, and potassium hydroxide (powder, 0.15 g) was added thereto and the mixture was stirred from 20 to 30° C. for 2 hours. Subsequently, ethylene diamine monohydrate (10.78 g, 138 mmol) was added thereto to terminate the reaction, and then toluene (46 mL) was added thereto to dilute. A 25% aqueous ammonia solution (20 mL) was added thereto to wash the organic phase four times and anhydrous sodium sulfate (4 g) was added to the organic phase to dry, followed by filtration. The filtrate was concentrated under a reduced pressure to obtain Compound 52 as transparent liquid.

Yield: 3.2 g

[Step (2')]

(53)

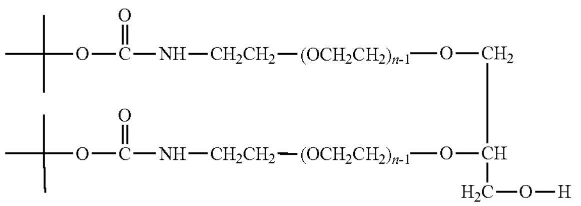

Compound 52 (3.0 g, 2.1 mmol), methanol (120 mL) and 5% Pd/C (1.5 g) were charged in an eggplant-shaped flask. The inside of the eggplant-shaped flask was purged with nitrogen, cyclohexene (4.1 g) was added thereto, and the mixture was stirred from 50 to 60° C. for 4 hours. After cooling to 30° C., chloroform (300 mL) was added thereto, the Pd/C was filtered off, and the filtrate was dried under a reduce pressure while adding toluene (100 mL) to finally substitute the solvent with toluene (40 mL). Anhydrous sodium sulfate (3 g) was added to the organic phase to dry, followed by filtration. The filtrate was concentrated under a reduced pressure to obtain Compound 53 as transparent liquid.

Yield: 2.2 g

[Step (3') to (4')]

(45)

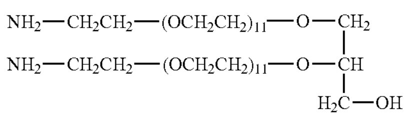

Compound 53 (2.0 g, 1.48 mmol) and dichloromethane (16 mL) were charged in an eggplant-shaped flask, and the inside of the eggplant-shaped flask was purged with nitrogen. Trifluoroacetic acid (3 g) was added thereto, and the mixture was stirred at room temperature for 2 hours. After 2 hours, the disappearance of Compound 53 was confirmed by thin layer chromatography (TLC) measurement and water (40 mL) was added to extract the desired compound into an aqueous phase. A small amount of an aqueous 400 g/L sodium hydroxide solution was added to the aqueous solution to adjust pH to 7.5 and sodium chloride was added thereto to form an aqueous saturated sodium chloride solution. Subsequently, chloroform (9 mL) and isopropanol (3 mL) were added thereto to extract the desired compound into the organic phase, and the organic phase was washed in order with an aqueous saturated sodium bicarbonate solution (20 mL) and an aqueous saturated sodium chloride solution (20 mL). The organic phase was concentrated under a reduce pressure, dissolved again in chloroform (20 mL), and sodium sulfate was added thereto to dry, followed by filtration. The filtrate was concentrated under a reduced pressure to obtain Compound 45 as transparent liquid. The molar yield of three steps based on Compound 50 was 51.8%. The chain length purity was 94.8% and the functional group purity was 98.2%.

Yield: 1.4 g

Example 8-2

Synthesis of Compound 54 Represented by Formula (1) Wherein $X^1$ is Maleimide Group, $Y^1$ is Active Carbonate Group and $L^3$ is Single Bond (55)

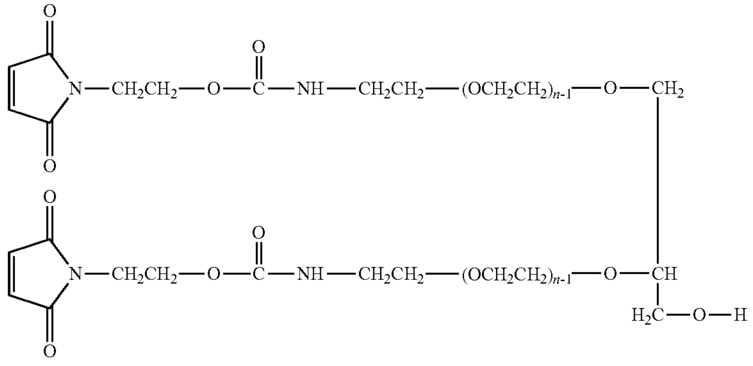

-continued (54)

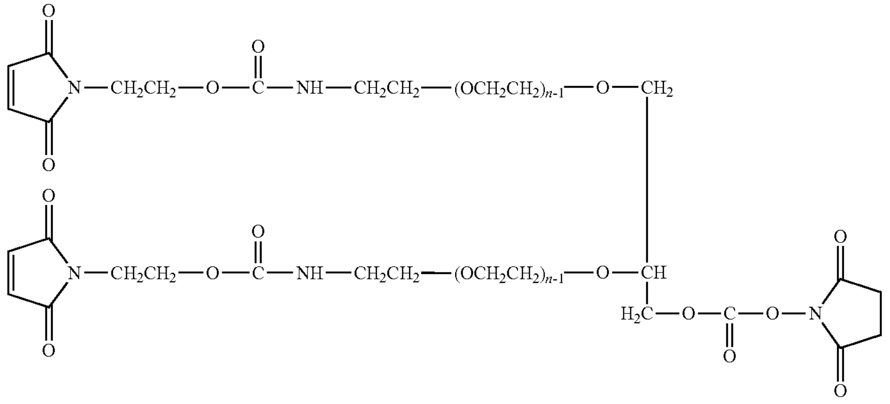

3-maleimidopropionic acid N-succinimidyl (667 mg, 2.5 mmol), dibutylhydroxytoluene (1 mg) and dichloromethane (130 mL) were charged in an eggplant-shaped flask. Compound 45 (1.2 g, 1.05 mmol) and triethylamine (0.38 mL, 2.7 mmol) were dissolved in dichloromethane (8 mL) and the solution was dropwise added to the flask at room temperature. After stirring at room temperature for 4 hours, the disappearance of Compound 45 was confirmed by thin layer chromatography (TLC) measurement, and the organic phase was washed three times with citric acid buffer (pH=3.0) containing 15% sodium chloride dissolved (50 mL) and concentrated under a reduced pressure. Citric acid buffer (pH=3.0) (50 mL) was added to the residue and the mixture was washed three times with toluene-dichloromethane (10:3 w/w) (50 mL). The aqueous phase was extracted three times with 50 mL of dichloromethane. The organic phases were put together, and anhydrous magnesium sulfate (1 g) was added thereto to dry, followed by filtration. The filtrate was concentrated under a reduced pressure to obtain Compound 55 as transparent liquid.

Yield: 890 mg

Compound 55 (780 mg, 0.54 mmol), triethylamine (0.12 mL, 0.86 mmol), dibutylhydroxytoluene (1 mg) and dichloromethane (15 mL) were charged in an eggplant-shaped flask. Disuccinimidyl carbonate (208 mg, 0.81 mmol) was added thereto, and the mixture was stirred at room temperature for 5 hours. After 5 hours, the disappearance of Compound 55 was confirmed by NMR measurement, citric acid buffer (pH=3.0) containing 15% sodium chloride dissolved (25 mL) was added to wash three times. The organic phases were put together and anhydrous sodium sulfate (1 g) was added thereto to dry, followed by filtration. The filtrate was concentrated under a reduced pressure to obtain Compound 54 as transparent liquid. The chain length purity was 93.2% and the functional group purity was 95.8%.

Yield: 705 mg.

The invention claimed is:

1. A method of producing a compound represented by formula (3):

(3)

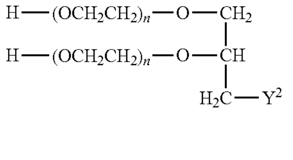

in formula (3), n represents an integer of 6 to 12, and $Y^2$ represents $-NH_2$ or $-O-(CH_2)_{m4}-NH_2$, and m4 represents an integer of 1 to 5, the method comprising:

step (1) of performing coupling of a monodispersed polyethylene glycol derivative represented by formula (4) shown below with a compound represented by formula (5) shown below using a base catalyst having a pKa in an aqueous solution of 15 to 20 to obtain a compound represented by formula (6) shown below, $$A\text{-}(OCH_2CH_2)_n\text{—}B \quad (4)$$

in formula (4),

A represents a protective group for a hydroxyl group,

B represents a leaving group, and n represents an integer of 6 to 12, (5)

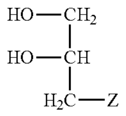

in formula (5),

Z represents $-Z^1$ or $-O-(CH_2)_{m5}-Z^1$, $Z^1$ represents any of a protected form of an amino group, an azide group and a cyano group, and m5 represents an integer of 1 to 5, (6)

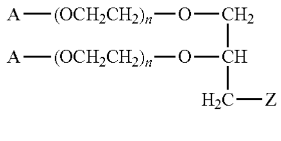

in formula (6),

A represents a protective group for a hydroxyl group,

Z represents $-Z^1$ or $-O-(CH_2)_{m5}-Z^1$, $Z^1$ represents any of a protected form of an amino group, an azide group and a cyano group, and m5 represents an integer of 1 to 5, and n represents an integer of 6 to 12;

step (2) of deprotecting the protective group A of the compound represented by the formula (6) to obtain a compound represented by formula (7) shown below, (7)

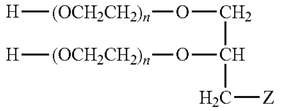

in formula (7),

Z represents $—Z^1$ or $—O—(CH_2)_{m5}—Z^1$, $Z^1$ represents any of a protected form of an amino group, an azide group and a cyano group, and m5 represents an integer of 1 to 5, and n represents an integer of 6 to 12;

step (3) of subjecting the compound represented by the formula (7) to separatory purification; and step (4) of subjecting the compound represented by the formula (7) to deprotection treatment or reduction treatment to obtain the compound represented by formula (3), in an order described above.

2. The method as claimed in claim 1, wherein the base catalyst is any of potassium hydroxide, sodium hydroxide, potassium tert-butoxide and sodium tert-butoxide.

3. A method of producing a compound represented by formula (40):

(40)

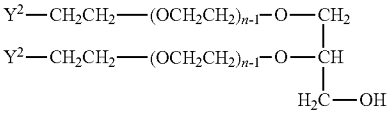

in formula (40), n represents an integer of 6 to 12, and $Y^2$ represents $—NH_2$ or $—O—(CH_2)_{m4}—NH_2$, and m4 represents an integer of 1 to 5, the method comprising:

step (1') of performing coupling of a monodispersed polyethylene glycol derivative represented by formula (41) shown below with a compound represented by formula (42) shown below using a base catalyst having a pKa in an aqueous solution of 15 to 20 to obtain a compound represented by formula (43) shown below, $$Z—CH_2CH_2—(OCH_2CH_2)_{n-1}—B \qquad (41)$$

in formula (41),

Z represents $—Z^1$ or $—O—(CH_2)_{m5}—Z^1$, $Z^1$ represents any of a protected form of an amino group, an azide group and a cyano group, and m5 represents an integer of 1 to 5, B represents a leaving group, and n represents an integer of 6 to 12, (42)

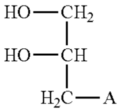

in formula (42),

A represents a protective group for a hydroxyl group, (43)

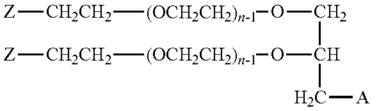

in formula (43),

A represents a protective group for a hydroxyl group,

Z represents $—Z^1$ or $—O—(CH_2)_{m5}—Z^1$, $Z^1$ represents any of a protected form of an amino group, an azide group and a cyano group, and m5 represents an integer of 1 to 5, and n represents an integer of 6 to 12;

step (2') of deprotecting the protective group A of the compound represented by the formula (43) to obtain a compound represented by formula (44) shown below, (44)

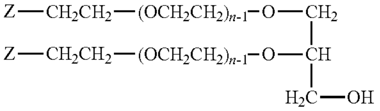

in formula (44),

Z represents $—Z^1$ or $—O—(CH_2)_{m5}—Z^1$, $Z^1$ represents any of a protected form of an amino group, an azide group and a cyano group, and m5 represents an integer of 1 to 5, and n represents an integer of 6 to 12;

step (3') of subjecting the compound represented by the formula (44) to deprotection treatment or reduction treatment to obtain the compound represented by formula (40); and step (4') of subjecting the compound represented by the formula (40) to separatory purification, in an order described above.

4. The method as claimed in claim 3, wherein the base catalyst is any of potassium hydroxide, sodium hydroxide, potassium tert-butoxide and sodium tert-butoxide.

* * * * *